United States Patent [19]

Nagasawa et al.

[11] 4,200,793
[45] Apr. 29, 1980

[54] DEVICE FOR SETTING REGION OF INTEREST FOR SCINTILLATION CAMERA

[75] Inventors: Yasuo Nagasawa; Junichi Yamada, both of Kashiwa, Japan

[73] Assignee: Hitachi Medical Corporation, Tokyo, Japan

[21] Appl. No.: 812,626

[22] Filed: Jul. 5, 1977

[30] Foreign Application Priority Data

Jul. 5, 1976 [JP] Japan ................................. 51-78928

[51] Int. Cl.² .............................................. G01T 1/20
[52] U.S. Cl. ................................................ 250/363 S
[58] Field of Search ........................... 250/363 S, 369; 128/2 A

[56] References Cited

U.S. PATENT DOCUMENTS 3,970,852  7/1976  Richey et al. .................... 250/363 S
4,013,878  3/1977  Wagner ......................... 250/363 S X Primary Examiner—Davis L. Willis
Attorney, Agent, or Firm—Wenderoth, Lind & Ponack

[57] ABSTRACT

The present invention is a device for setting a region of interest for a scintillation camera. It is employed for determining whether or not the coordinate signals X and Y which represent the positions of incident gamma rays are located within a specified region which is set by designating arbitrary positions and shape(s) on a rectangular coordinate system provided on the visual field of a camera. This device includes a region setting circuit for discriminating whether the coordinate signals X and Y are located within the specified region through comparison of the potential of the sum of the square of the values of the coordinate signals X and Y with a reference voltage.

25 Claims, 30 Drawing Figures

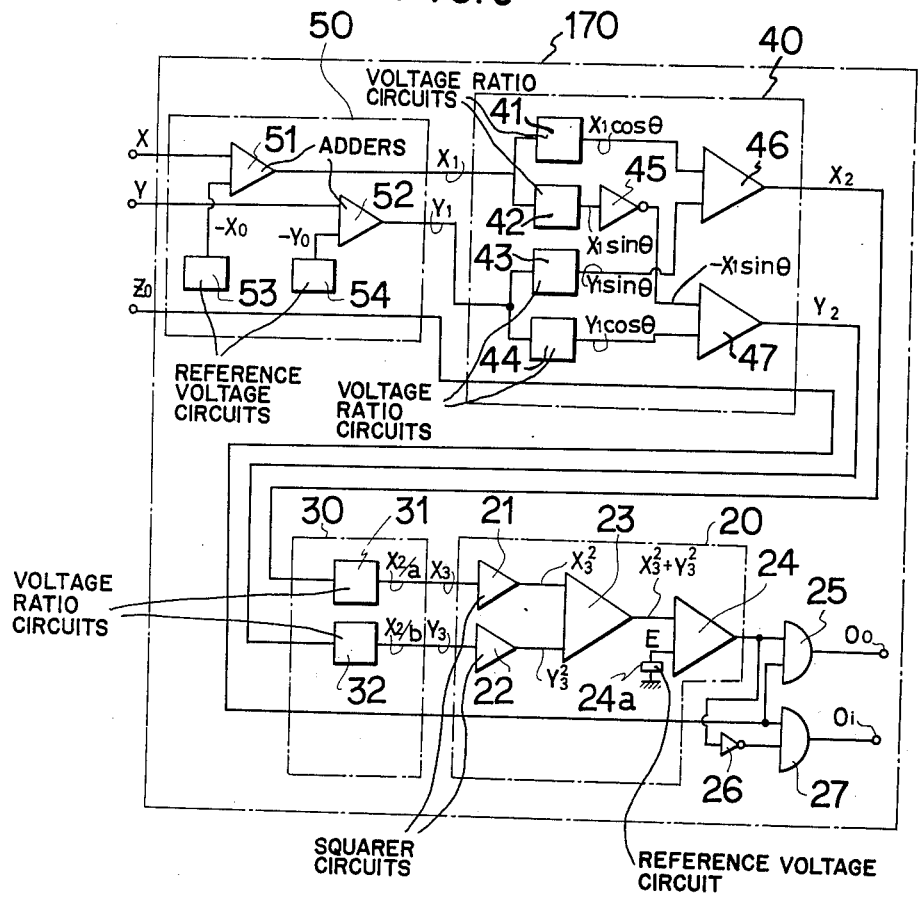
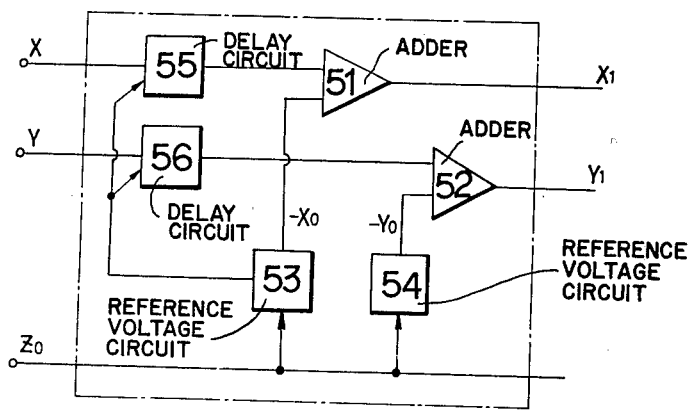

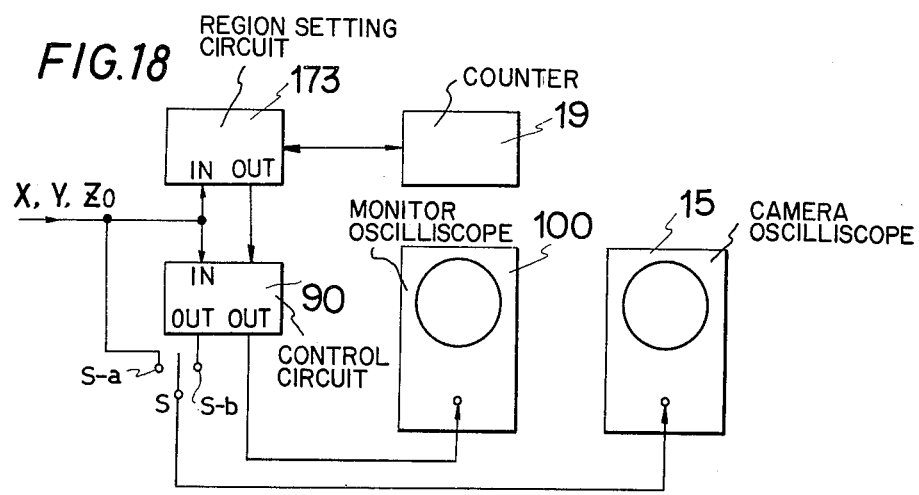
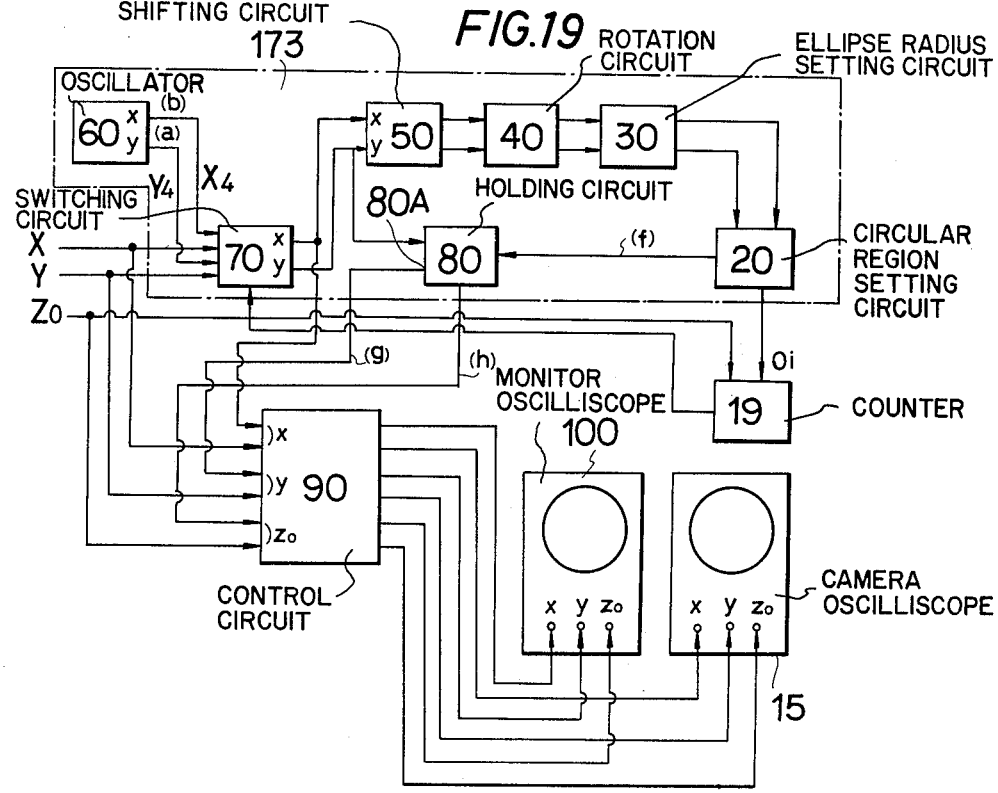

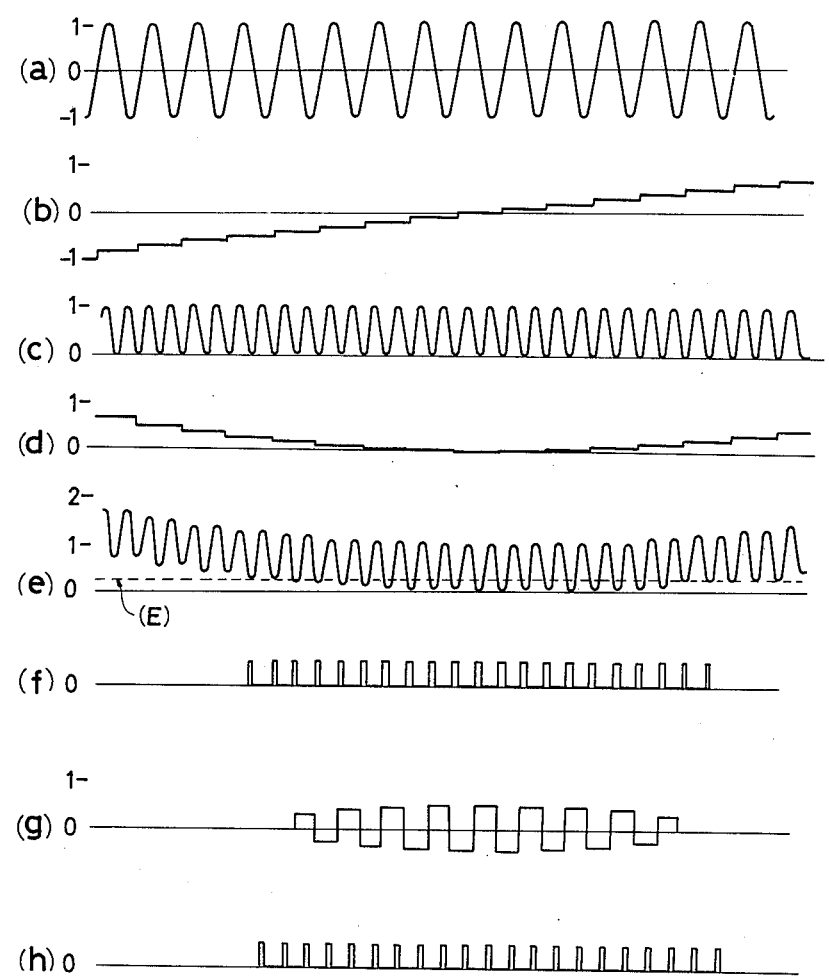

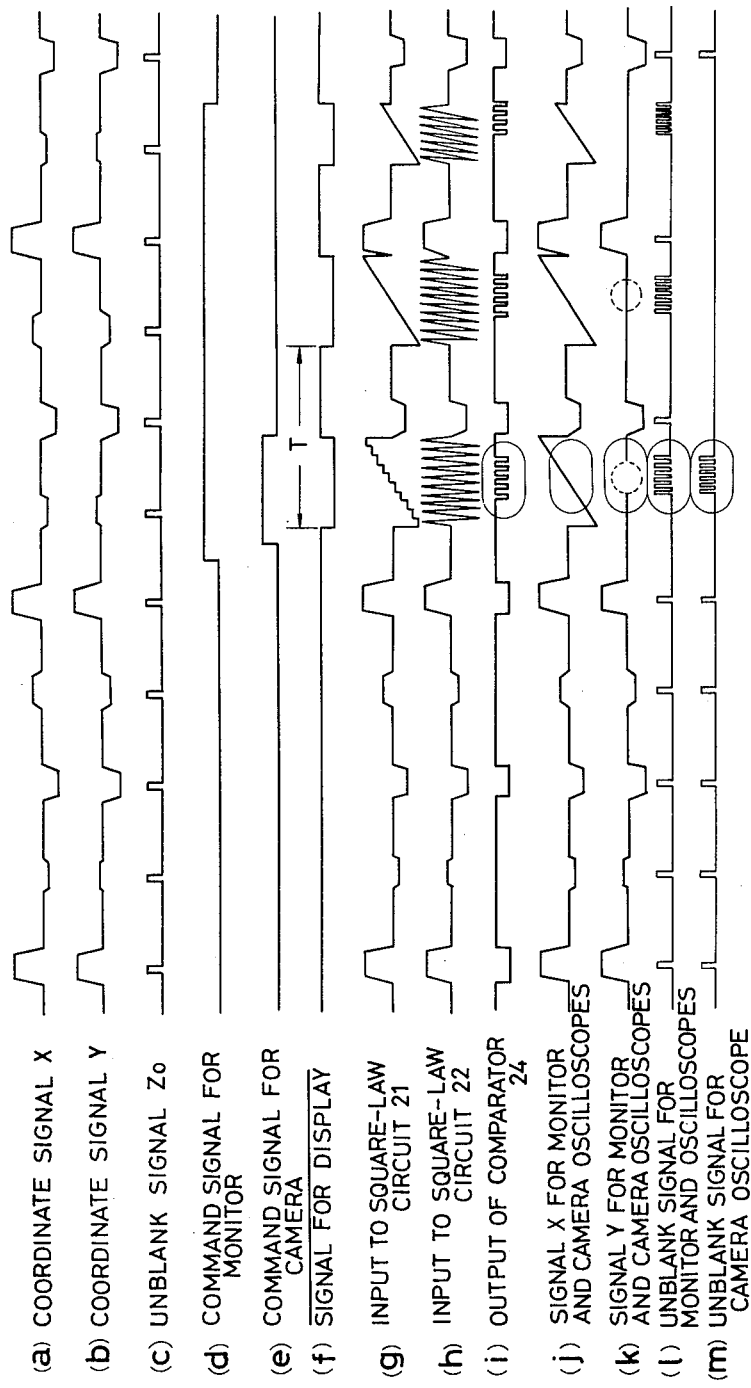

DEVICE FOR SETTING REGION OF INTEREST FOR SCINTILLATION CAMERA

BACKGROUND OF THE INVENTION (a) Field of the Invention

The present invention relates to a scintillation camera, and more particularly, it pertains to a device for designating a region of interest for a scintillation camera.

(b) Description of the Prior Art

Scintigram-producing apparatuses intended for measuring and recording an image representing the distribution of a radioactive isotope administered in a human body, i.e. the so-called scintillation camera, are widely used in the medical field as a means for making a diagnosis of a patient. It has been the practice in scintillation cameras of the prior art to set a desired region within the visual field of the camera, and to measure the count of gamma rays which are incident onto this set region. A means for a discriminating the presence or absence of the incident gamma rays within the set region is called a device for setting a region of interest for scintillation camera.

In such a device for setting a region of interest for a scintillation camera, it is known to be desirable to insure an exact agreement between the set region and the configuration of the specific part of the organ which is the object of measurement.

Organs of human beings have configurations which are generally close to either a circle or an ellipse. Thus, for example, if the region which is set on the camera is rectangular, it is not possible to perform a correct setting of a region so as to be in conformity with the actual shape of the objective organ. The discrepancy which arises between the circular or elliptic shape of the organ and the rectangular region which is set for the camera will bring about a measurement error when comparison is made between the radiation intensities in the objective portion of the organ and the radiation intensities in the areas surrounding this objective portion. For example, let us assume that a rectangular region is set over a kidney which actually has a configuration resembling that of a broad bean. Then, the portion of the region occupied by the configuration of the kidney within the rectangular region will be of the order of only 70–80% at the greatest. The remaining 30–20% portion is located outside the boundary of the kidney. The radiation intensities in those regions located outside the kidney are low. Thus, there arises a substantial error or discrepancy between the total count of the mean radiation intensity of gamma rays located within the rectangular region and the actual total count of the mean radiation intensity of gamma rays in the region of the kidney.

A major problem which is encountered in known devices for setting a region of interest for a scintillation camera is that it is not possible to set a region for the scintillation camera in a manner faithful to the actual selected portion of the given organ, and that accordingly there arises a discrepancy between the value of measurement and the actual count of gamma rays.

SUMMARY OF THE INVENTION

It is, therefore, a primary object of the present invention to provide an improved device for setting a region of interest for a scintillation camera.

Another object of the present invention is to provide a device of the type as described above, which allows a circular or elliptic region of interest to be set, and which furthermore allows the position of the ellipse, the dimensions of the longer and the shorter diameters of the ellipse, as well as the inclination of the ellipse to be altered as desired, thereby enabling one to set a precise region of interest.

These and other objects as well as the attendant features and advantages of the present invention will become apparent by reading the following detailed description when taken in conjunction with the accompanying drawings.

BRIEF DESCRIPTION OF THE DRAWINGS

FIG. 3 to FIG. 5 show an example of the device of the present invention, in which:

FIG. 3 is a circuit diagram showing the entire arrangement of the device;

FIG. 4 is an explanatory illustration concerning a specific region of interest for the device shown in FIG. 3; and FIG. 5 is a circuit diagram, showing the details of the circuit illustrated in FIG. 3.

FIG. 6 to FIG. 11 show a further example of the device of the present invention, in which:

FIG. 6 is a circuit diagram, showing the entire arrangement of the device;

FIG. 7 is a circuit diagram, showing a modification of a part of the circuit shown in FIG. 6;

FIG. 8 is a circuit diagram, showing the details of a part of the circuit shown in FIG. 6, i.e. the details of the coordinate system shifting circuit;

FIG. 9 and FIG. 10 are explanatory illustrations concerning the manner in which a region of interest is set in the device; and FIG. 11 is a circuit diagram, showing the details of another part of the circuit shown in FIG. 6, i.e. the details of the rotation circuit.

FIG. 12 to FIG. 17 show modifications of the device shown in FIG. 6 to FIG. 11, in which:

FIG. 12 is a block diagram, showing the entire arrangement of a modification of the device;

FIG. 13 is an explanatory illustration showing the manner in which a region of interest is set, in the modification of FIG. 12; and FIG. 14 to FIG. 17 are explanatory illustrations showing the manner in which a region of interest is set in stilll further modifications, respectively.

FIG. 18 to FIG. 30 show a still further example of the device according to the present invention, in which:

FIG. 18 is a block diagram, showing the entire arrangement;

FIG. 19 is a more detailed block diagram of the block diagram shown in FIG. 18;

FIG. 20 is an illustration, showing a series of waveshapes and pulses for explaining the operation of a part of the circuit shown in FIG. 19;

FIG. 21 to FIG. 25 can be illustrations for explaining various different regions of interest which can be depicted on the monitor oscilloscope in the device of this example;

FIG. 26 is an illustration, showing a series of waveshapes and pulses for explaining the operation of a part of the circuit of FIG. 19, i.e. the operation of the control circuit;

FIG. 27 is a circuit diagram, showing the details of a part of the circuit shown in FIG. 19, i.e. the details of the oscillator circuit;

FIG. 28 is a circuit diagram of another part of the circuit shown in FIG. 19, i.e. the details of the switching circuit and the holding circuit; and FIG. 29 is a circit diagram, showing an example of a circuit for generating a signal to cause the indication of the boundary; and FIG. 30 is an illustration, showing a series of waveshapes and pulses to assist the understanding of the operation of the device as a whole shown in FIG. 18 and FIG. 19.

DETAILED DESCRIPTION OF THE PREFERRED EMBODIMENTS

Figure 1:
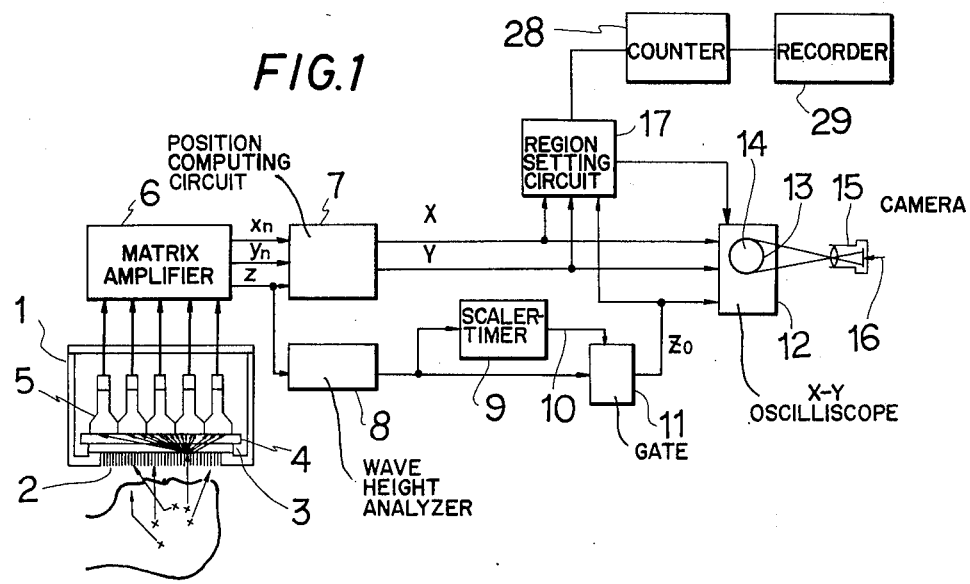
FIG. 1 is a block diagram, showing the entire arrangement of the scintillation camera equipped with the device for setting a region of interest according to the present invention.

FIG. 1 is a block diagram of a scintillation camera equipped with the device for setting a region of interest according to the present invention.

Gamma rays which are emitted from the radioactive isotope distributed in a human body impinge onto the scintillator 3 via collimeter 2 of detector 1. By this arrangement, only those incident gamma rays which are parallel to the direction of the slits of the collimeter 2 are allowed to reach the scintillator 3. Those gamma rays which impinge onto the scintillator 3 are absorbed there and luminesce. The intensity of luminescence is proportional to the energy of the incident gamma rays. The beams of light are led to photomultiplier tubes 5 via guide 4. The respective photomultiplier tubes 5 generate pulse signals having wave heights proportional to the intensity of the incident beams of light. Accordingly, those photomultiplier tubes 5 which are located in the vicinity of the positions at which the gamma rays impinge will generate strong signals. However, the outputs of those photomultiplier tubes which are located far from the spots of incidence of the gamma rays are small. It is possible, therefore, to obtain the positions of the incident gamma rays by the comparison of the magnitudes of these signals.

Figure 2:
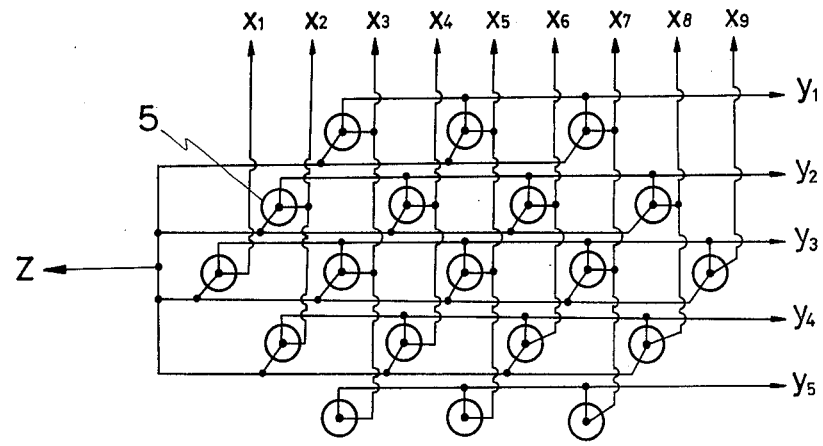
FIG. 2 is an explanatory representation for showing the manner in which the outputs of the two-dimensionally arranged photoelectric amplifying tubes are summed, in the abovesaid scintillation camera.

In an actual scintillation camera, in order to obtain the position of an incident gamma ray on a two dimensional basis, there are arranged a number of photomultiplier tubes in a closely adjacent honey-comb fashion. More specifically, as shown in FIG. 2, the signals from the photomultiplier tubes arranged in each column in the X direction are summed by the matrix amplifier 6 to prepare column signals $x_1$-$x_9$. Similarly, the signals from the photomultiplier tubes arranged in each row in the Y direction are summed by the matrix amplifier 6 to prepare row signals $y_1$-$y_5$. The magnitudes of the respective signals $x_1$-$x_9$ and $y_1$-$y_5$ are compared in a position computing circuit 7 to compute the positions of the incident gamma rays to prepare coordinate signals X and Y.

On the other hand, a signal Z is prepared by summing the output signals of all the photomultiplier tubes. This signal Z has a magnitude proportional to the energy of the incident gamma rays. This signal Z is led to the wave height analyzer 8. The wave height analyzer 8 triggers the scaler-timer 9 only when the signal supplied to the wave height analyzer 8 has a magnitude corresponding to the energy of the gamma rays radiated from the objective radioactive isotope. Whereupon, this scaler timer 9 generates control signal 10 which, in turn, opens gate 11. Thereby, the wave height analyzer 8 generates the unblank signal $Z_0$.

The signals X and Y as well as the unblank signal $Z_0$ which are formed in the manner stated above are coupled to the X and Y deflection circuits and the unblank circuit of an X-Y oscilloscope 12, to form luminous spots 14 in the Braun tube 13 of the X-Y oscilloscope 12 at positions corresponding to the positions of the incident gamma rays.

In the manner described above, the luminous spots corresponding to the positions of the incident gamma rays which successively impinge onto the scintillator are photographed by a camera 15. By printing these luminous spots on film 16, it is possible to record a distribution image of the radioactive isotope contained within the body of the patient, i.e. it is possible to prepare a scintigram.

The gamma rays which are radiated from the radioactive isotope distributed in the body of the patient are divided into the following two categories, i.e. those impinging directly onto the scintillator and those scattering within the patient's body and then impinging onto the scintillator. Those gamma rays which scatter in the patient's body have to be ruled out since they would supply to the scintigram erroneous information as if the sources of radiation were located at the sites whereat the scattering of the gamma rays took place. When a gamma ray scatters, it loses a part of its energy. Accordingly, the signal Z which is formed by those gamma rays which are incident to the scintillator after scattering within the patient's body has a magnitude which is substantially smaller than that of the signal formed by those gamma rays which are directly incident to the scintillator from the radioactive isotope distributed within the patient's body.

The wave length analyzer 8 generates the unblank signal $Z_0$ only for a signal Z of a predetermined magnitude, as stated previously. Therefore, this analyzer 8 serves to eliminate those luminous spots produced by scattered gamma rays.

The scaler-timer 9 is employed to control the conditions for photographing, onto film, those luminous spots produced on the Braun tube of the X-Y oscilloscope 12. More specifically, the scaler-timer controls the time of exposure and the number of luminous spots.

In such a scintillation camera as described above, the following operations are conducted. Namely, a specific portion within the visual field of the scintillation camera is selected; the number of the gamma rays present in that specific portion is counted; the counted number is compared with the number of gamma rays falling in other portions; and the total number of gamma rays detected in said specific portion relative to the total amount of the radioactive substance administered into the patient's body is measured. The particular means for discriminating whether or not the signal X and the signal Y indicate that the position of the gamma rays lies within the area (region) of interest is the device for setting a region of interest for a scintillation camera, designated by 17. The gamma rays which have been thus discriminated by this device 17 are counted by the counter 28 and are displayed, and the count recorded in the recorder 29, such as a pen recorder, as required.

Figure 3:
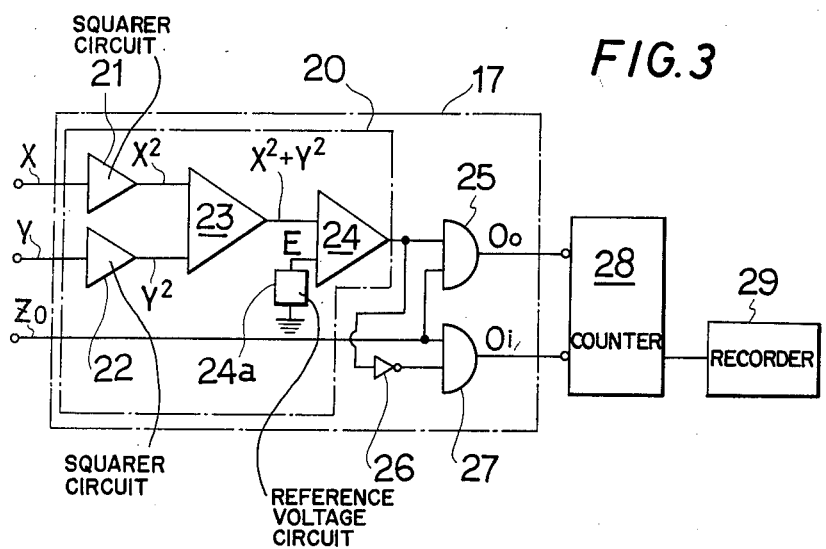
Figure 4:
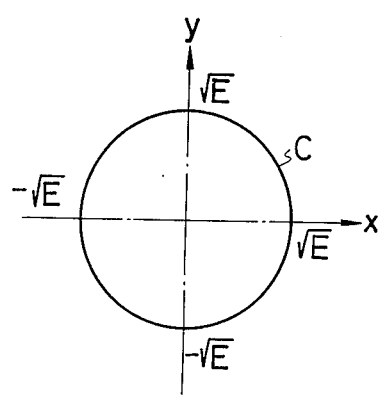
Figure 5:
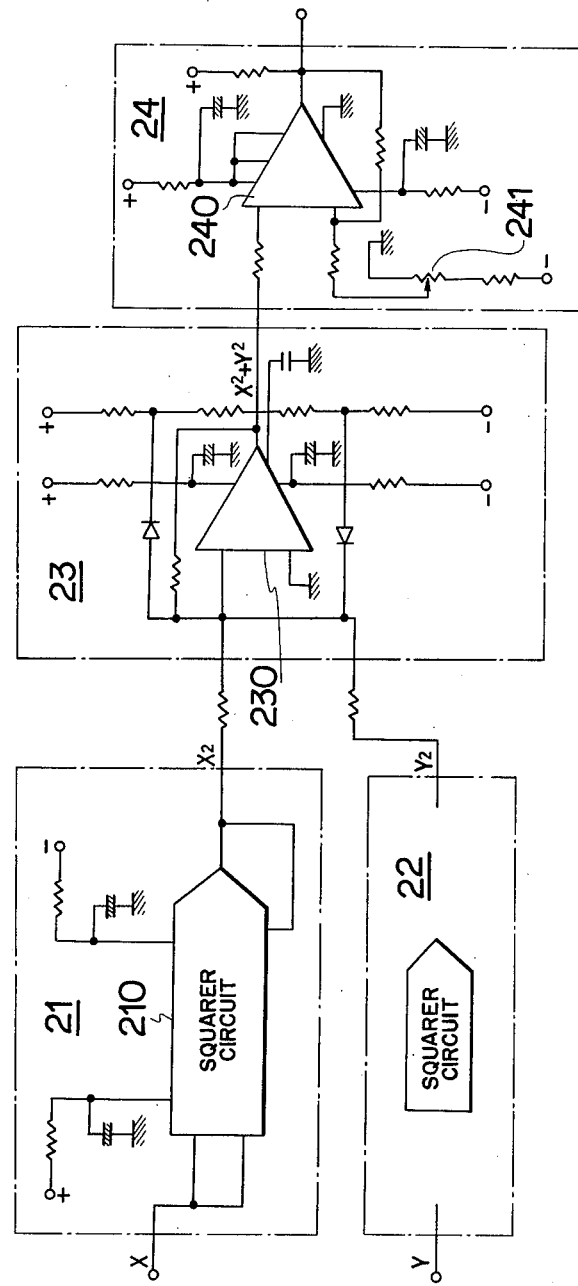

FIGS. 3-5 show an example of the device for setting a region of interest for a scintillation camera according to the present invention. Those figures show a circuit for carrying out the setting of a circular region of interest about the coordinate origin and for carrying out the discrimination. In FIG. 3, the signals X and Y represent signals showing the positional coordinates of gamma rays which have been prepared in the position computing circuit 7 of FIG. 1. These signals have wave heights proportional to the positional coordinates, and have either positive, negative or zero waveshapes. Symbol $Z_0$ represents the unblank signal which is the output of the gate 11 shown in FIG. 1, and has in the form of a pulse wave with a predetermined wave height associated with a predetermined lapse of time, in synchronization with the signals X and Y. Accordingly, in case either or both of the signals X and Y generate(s) an output of zero wave height and the signal $Z_0$ is generated synchronously, this indicates that the position of the gamma ray which is incident to the scintillator 3 is located either on the origin of the rectangular coordinate system, or on the X axis or Y axis.

The signals X and Y which have entered into a circular region setting circuit 20 are first subjected to a squaring operation in the squaring operation circuits 21 and 22, respectively, to become signals $X^2$ and $Y^2$, respectively. These signals are then supplied to the adder circuit 23 connected to the output side of the squaring operation circuits, wherein an addition is performed and a signal with a value of $X^2+Y^2$ is generated. Note that the signals X and Y which are received from the position computing circuit 7 are received in synchronism. Accordingly, the signal which is generated by the adder circuit 23 is in the form of a pulse wave having a wave height of $X^2+Y^2$. This output signal is applied to a comparator circuit 24 which is connected to the adder circuit, and its potential is compared therein with a reference voltage E supplied from a reference voltage generating circuit 24a. When, $$X^2+Y^2 \geq E \qquad (1)$$

the comparator circuit 24 generates an output with a logic level "1". In case, however, the relation is $$X^2+Y^2 < E \qquad (2),$$

an output with a logic level "0" is generated.

In case the coordinate signals X and Y which have been received from the position computing circuit 7 lie within the circular region of radius $\sqrt{E}$ centering around the origin of the rectangular coordinate system, the output of the comparator circuit 24 has a logic level of "0". In case the signals X and Y lie outside of the circular region of radius $\sqrt{E}$, the output of the comparator circuit 24 will have a logic level of "1". Accordingly, applying the signal produced by the comparator circuit 24 and the unblank signal $Z_0$ into the AND circuit 25, there is produced by this AND circuit 25, which is connected to the output side of the comparator circuit 24, a signal $O_0$ which indicates that the detector 1 has produced a signal the coordinates of which lie either on or outside of a circle C of the radius $\sqrt{E}$ centering around the origin of the rectangular coordinate system of the scintillator 3, as shown in FIG. 4. In such an instance, the AND circuit 25 is not necessarily needed. However, in view of the fear that an erroneous signal could be delivered from the comparator circuit 24 owing to a slight difference in the build-up times of the pulses of the signals X and Y or to the possible delay in the computation performed in the squaring operation circuits 21 and 22, it is preferred that this AND circuit be provided in order to eliminate such an erroneous signal. On the other hand, in case the positional signal produced by the position computing circuit 7 lies within the region of this circle, the output of the comparator circuit 24 has a logic level of "0". Therefore, this output is applied to the AND circuit 27 which is connected to the output side of the signal inverting circuit 26 which, in turn, is connected in parallel with the AND circuit 25. Thus, by taking an AND with the unblank signal $Z_0$, there is produced by the AND circuit 27 a signal $O_i$ which indicates that the positional coordinate lies within the circular region. In case it is desired to alter the size of the region of interest, it is necessary to alter the reference voltage E.

Accordingly, by counting the number of the pulses of the signal $O_i$ produced by the AND circuit 27 for predetermined intervals in the counter 28 and also by recording the count on recorder 29 or printing out the count by a printing means, it is possible to obtain the number of the gamma rays that were produced within the set region. Furthermore, by conducting counts for a number of predetermined intervals of time in the counter 28 and by recording the respective counts successively on the recorder 29, it is possible also to follow up the variation of the number of gamma rays produced within the specific region. It is possible to use an analog-type integrating circuit in place of the counter 28.

FIG. 5 shows an example of a more concrete circuit which may be used as squaring operation circuit 21, adder circuit 23 and comparator circuit 24. In the figure, the squaring operation circuit 22 has a construction identical with the squaring operation circuit 21. Therefore, its detailed explanation is omitted. The squaring operation circuit 21 includes a squarer 210 which uses two inputs for the signal X, and an output of $X^2$ is obtained therefrom. By taking into consideration the fact that the time length of the signals X is very short, being 2-3 microseconds in general, it is necessary to choose a squarer which has a quick response, in order to minimize signal delay. This same limitation holds true for the squaring operation circuit 22. The adder circuit 23 comprises an operational amplifier 230. The arrangement is such that the respective output signals $X^2$ and $Y^2$ from the squaring operation circuits 21 and 22 which carry out said squaring operations are received with by one of the input sections of the operational amplifier 230 via a resistor, so that a signal with a value of $X^2+Y^2$ is obtained. The comparator circuit 24 comprises an operational amplifier 240 and is arranged so that said the signal $X^2+Y^2$ is applied to one of the inputs of this operational amplifier 240, and that a reference voltage which is adjustable by a variable resistor 241 is applied to the other of the input sections. This comparator circuit 24 generates a signal having a logic level of "1" when $X^2+Y^2 \geq E$, and a signal having a logic level of "0" when $X^2+Y^2 < E$.

FIG. 6 to FIG. 11 show another example of the device for setting a region of interest according to the present invention. In this instant device, it is possible to set a circular or an elliptic region of interest. Furthermore, this device is arranged so that the position of the circle, the dimensions of the longer and the shorter diameters of the ellipse and also the inclination of the ellipse may be altered as desired, to perform the setting of a region of interest with a further enhanced level of precision.

The device of this example comprises: a coordinate system shifting circuit 50; a rotation circuit 40 for rotating the coordinate system to obtain an elliptic region of interest; an ellipse radius setting circuit 30; a circular region setting circuit 20; the AND circuits 25, 27 and signal inverting circuit 26.

A description will first be made with respect to the coordinate system shifting circuit 50.

Figure 9:
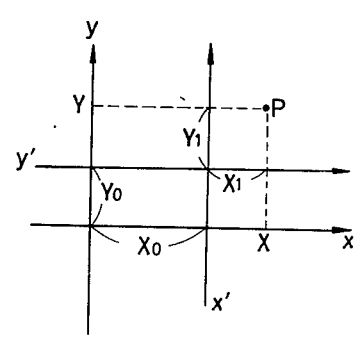

The operation of this coordinate shifting circuit 50 is clearly shown in FIG. 9. More specifically, by setting substantially new coordinates x' and y' relative to the original coordinate system x and y, the coordinates of point P are changed, by the shifting of said coordinate system, from (X, Y) to ($X_1$, $Y_1$).

Shifting of the position of a specific region of interest can be realized by a parallel translation of that coordinate system which uses the center of the scintillator 3 shown in FIG. 1 as the origin of coordinates. More particularly, from the magnitudes of the coordinate signals X, Y which are produced by the position computing circuit 7 of FIG. 1 are subtracted the voltages $X_0$, $Y_0$ corresponding to the distance to which the coordinates are to be translated parallelly in accordance with the following Equations (3) and (4), respectively. The resulting signals $X_1$ and $Y_1$ are used as the new coordinate signals.

$$X_1 = X - X_0 \tag{3}$$

$$Y_1 = Y - Y_0 \tag{4}$$

In the coordinate system shifting circuit 50, reference numerals 53 and 54 represent circuits for producing the signals $-X_0$ and $-Y_0$ for use in carrying out the subtraction. The voltages of these signals $-X_0$ and $-Y_0$ may be produced by dividing the voltage of a DC power source by a resistor-type voltage divider. These signals are applied to one of the input terminals of the adder circuits 51 and 52, respectively, and the coordinate signals X and Y from the position computing circuit 7 of FIG. 1 are applied to the other input terminals of the adder circuits 51 and 52, respectively. Thus, the operations of the Equations (3) and (4) are carried out. The aforesaid explanation has been made on the basis that the signals $-X_0$ and $-Y_0$ which are subjected to addition are DC signals. In case, however, these signals $-X_0$ and $-Y_0$ are required to be pulse signals which are synchronous with the coordinate signals X and Y, it is only necessary that, as shown in FIG. 7, the delay circuits 55 and 56 are included or that pulse peak holding circuits is provided in the stage preceding the adder circuits 51 and 52, which are triggered by the signal $Z_0$ so that the signals $X_1$ and $Y_1$ are formed without destroying the timing relation of the signals X, Y and Z.

Figure 8:
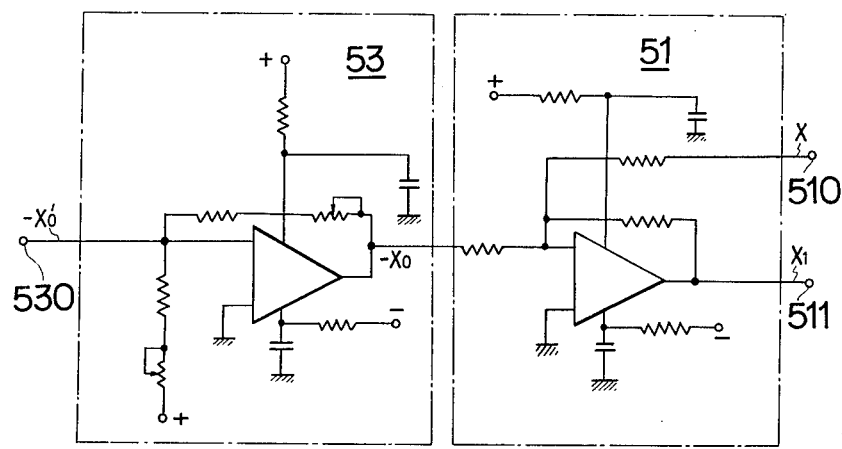

FIG. 8 shows an example of the adder circuit 51 and the circuit 53 for setting the signal $-X_0$ which are shown in FIG. 6. The circuit 53 is a circuit for producing the above-said signal $-X_0$ by arbitrarily setting a signal $-X'_0$ at the input terminal 530. As the means for changing the signal $-X'_0$, number of resistors having different resistance values are provided in parallel between the terminal not shown of a negative power source and the input terminal 530, and a desired resistor is connected to the input terminal 530 by means of a switch. To the input terminal 510 of the adder circuit 51 is applied the signal X from the position computing circuit 7, so that there is obtained the signal $X_1$ of $X - X_0$. The adder circuit 52 and the circuit 54 correspond to the adder circuit 51 and the circuit 53 shown in FIG. 8, respectively.

Figure 10:
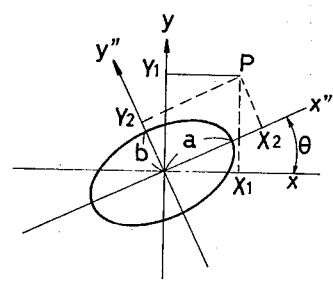

Returning here again to FIG. 6, an explanation will be made with respect to the rotation circuit 40. This rotation circuit 40 is intended, in case an elliptic region of interest is to be set by the ellipse radius setting circuit 30, to set a new coordinate system x'' and y'' which is produced by rotating the elliptic region through an angle of $\theta$ from the original coordinate system x and y as shown in FIG. 10, to thereby change the coordinates ($X_1$, $Y_1$) to ($X_2$, $Y_2$), respectively. As this rotation circuit 40, there is shown in the example a circuit which is capable of rotating the coordinate system through an angle $\theta$ from 0 degrees to 90 degrees.

In the rotation circuit 40 shown in FIG. 6, reference numeral 41 represents a voltage divider for obtaining $X_1 \cos \theta$ from the signal $X_1$ which is received from the coordinate system shifting circuit 50. Numeral 42 represents a voltage divider for obtaining $X_1 \sin \theta$ from the signal $X_1$. Numeral 43 represents a voltage divider for obtaining $Y_1 \sin \theta$ from the signal $Y_1$. Numeral 44 represents a voltage divider for obtaining $Y_1 \cos \theta$ from the signal $Y_1$. Numeral 45 represents an inverting amplifier having a gain of 1. Numeral 46 represents a summing amplifier for obtaining from the output signals of the voltage dividers 41 and 43:

$$X_2 = X_1 \cos \theta + Y_1 \sin \theta \tag{5}$$

Numeral 47 represents a summing amplifier for obtaining from the output signals of the inverting amplifier 45 and the voltage divider 44:

$$Y_2 = -X_1 \sin \theta + Y_1 \cos \theta \tag{6}$$

By a rotation circuit as described above, it will be apparent that signals $X_2$ and $Y_2$ which represent changed coordinate axes can be obtained. By arranging the voltage dividers 41-44 so as to be a combination of 4 series of rotary switches and a plurality of voltage-dividing resistors, it is possible to alter the angle $\theta$ which is to be set by steps.

Figure 11:
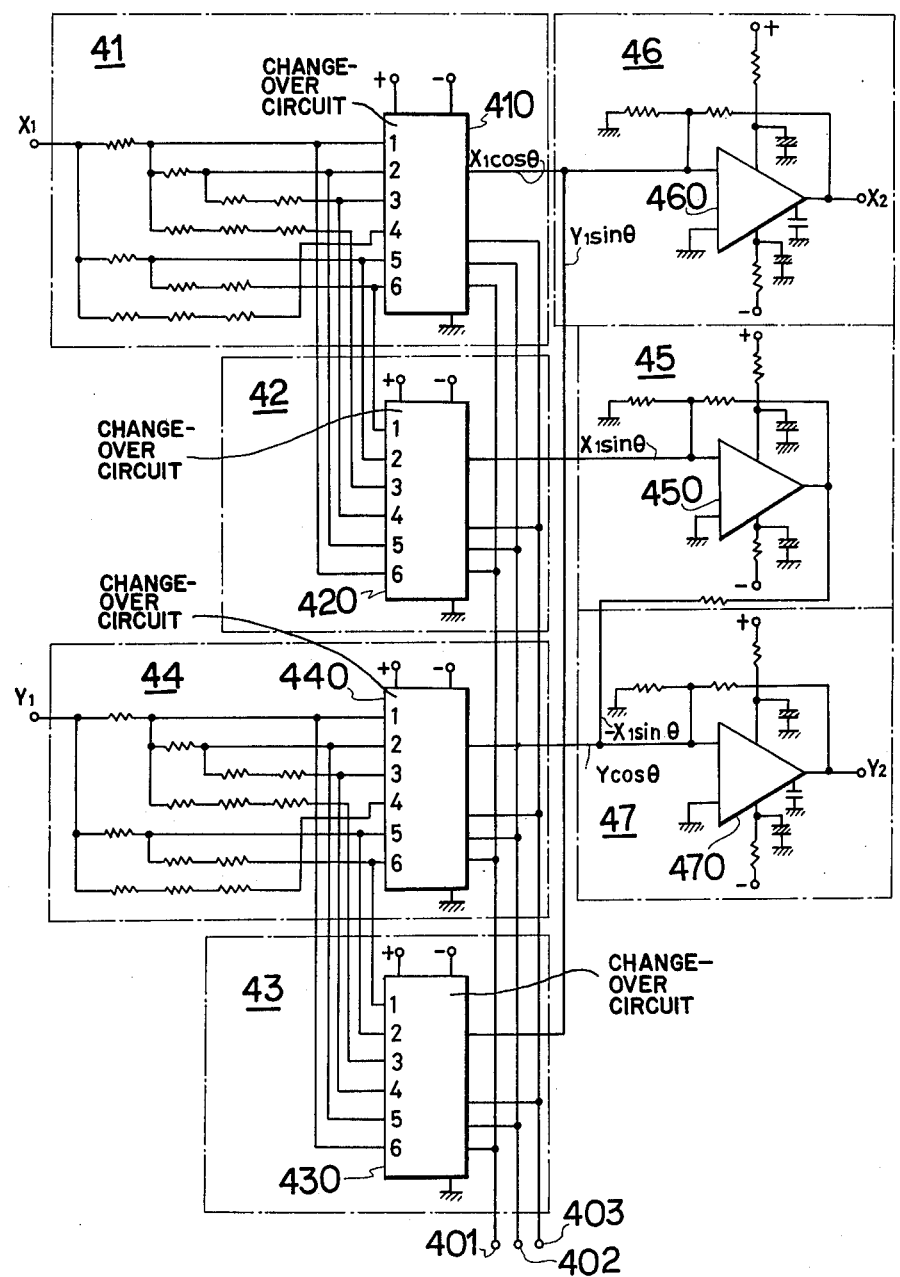

FIG. 11 shows a concrete example of the aforesaid rotation circuit 40. There are provided changeover circuits 410, 420, 430 and 440 which are operative so that by the application of coded changeover signals from changeover signal input terminals 401, 402 and 403 to the voltage dividers 41-44, respectively, one of the 6 rows of resistors is selected. In this instance, the 6 rows of resistors have resistance values which represent 0 degrees, 15 degrees, 30 degrees, 45 degrees, 60 degrees and 74 degrees, respectively. The arrangement among the input terminals 1-6 of the changeover circuits 410 and 420, where the input resistors are connected in common, utilizes the relationship:

$$\sin \theta = \cos (90° - \theta)$$

This holds true also for the relationship between the changeover circuits 430 and 440. The summing amplifiers 46 and 47 and the inverting amplifier 45 are circuits which use operational amplifiers 460, 470 and 450, respectively. In the summing amplifiers 46, the output signal $X_1 \cos \theta$ of the voltage divider 41 and the output signal $Y_1 \sin \theta$ of the voltage divider 43 are joined at the input section of the amplifier 46 to obtain the signal $X_2$ of Equation (5). Also, in the summing amplifier 47, the output signal $Y_1 \cos \theta$ of the voltage divider 44 and the signal $-X_1 \sin \theta$ which is an inverted output signal $X_1$ sin θ of the voltage divider 42 are summed to obtain the signal Y₂ of the Equation (6).

In FIG. 6 and FIG. 11, there have been shown examples in which the angle to be set is varied through the range of from 0 degrees up to 90 degrees. In case it is intended to vary the angle through the range of from 0 degrees to 180 degrees, it is only necessary to provide an inverting amplifier which is capable of inverting the output signal Y₁ sin θ of the voltage divider 43 for the range θ of from 90 to 180 degrees, so that when the θ is in the range of 90 to 180 degrees, the signal X₂ is obtained by the operation of the following Equation (7), and that without inverting the output signal of the voltage divider 42, the signal Y₂ is obtained by the operation of the following Equation (8):

$$X_2 = X_1 \cos\theta - Y_1 \sin\theta \quad (7)$$

$$Y_2 = X_1 \sin\theta + Y_1 \cos\theta \quad (8)$$

Next, a description will be made with respect to the ellipse radius setting circuit 30 illustrated in FIG. 6. Reference numerals 31 and 32 represent dividing circuits for dividing the signals X₂ and Y₂ from the rotation circuit 40 in accordance with the following Equations (9) and (10) to obtain the signals X₃ and Y₃, respectively:

$$X_3 = X_2/a \quad (9)$$

$$Y_3 = Y_2/b \quad (10)$$

Such dividing circuits as stated above may be realized using either a resistance-type voltage divider or a variable gain type amplifier. Therefore, the explanation of their detailed circuits is omitted. It should be noted that the symbols a and b in Equations (9) and (10) represent one half of the longer diameter a and one half of the shorter diameter b of the set ellipse shown in FIG. 10, respectively.

The signals which are applied to the circular region setting circuit 20 are: X₂/a and Y₂/b. Therefore, the comparing operation in the comparator circuit will be: in the case where $$(X_2/a)^2 + (Y_2/b)^2 \geq E \quad (11),$$

the logic level of the output signal of the comparator circuit 24 becomes "1", whereas in the case $$(X/a)^2 + (Y_2/b)^2 < E \quad (12),$$

the logic level of the output signal of the comparator circuit 24 will become "0".

When Equations (5) and (6) are substituted into the left side of the Equation (11), there is obtained the following relation:

$$\left(\frac{X_1\cos\theta + Y_1\sin\theta}{a}\right)^2 + \left(\frac{-X_1\sin\theta + Y_1\cos\theta}{b}\right)^2 \geq E \quad (13)$$

Furthermore, when Equations (3) and (4) are substituted into the Equation (13), there is obtained the following formula:

$$\left\{\frac{(X-X_0)\cos\theta + (Y-Y_0)\sin\theta}{a}\right\}^2 + \quad (14).$$

-continued
$$\left\{\frac{-(X-X_0)\sin\theta + (Y-Y_0)\cos\theta}{b}\right\}^2 \geq E$$

Accordingly, in the comparator circuit 24, the value (which will be referred to as E₀) of the signal on the left side of the Equation (14) is compared with the reference voltage E. When $$E_0 \geq E \quad (15),$$

the output O₀ of the AND circuit 25 becomes "1", and when $$E_0 < E \quad (16),$$

the output O₍ᵢ₎ of the AND circuit 26 becomes "1".

Equations (14), (15) and (16) show that it is possible to set an elliptic region of interest having an arbitrary size, an arbitrary inclination and an arbitrary radius at an arbitrary position, and to perform a discriminating operation as to whether or not the coordinate signals X and Y fall inside or outside of the set region of interest, and to indicate the result of this discrimination.

Furthermore, it is also possible to set a plurality of regions of interest independently of each other by the provision of a plurality of the aforesaid region-setting circuits 50, 40, 30 and 20. By applying the output signals of these plural region-setting circuits to an OR circuit or to an AND circuit, it becomes possible to set a region of interest having a synthesized configuration of circular or ellipsoidal sections.

Figure 12:
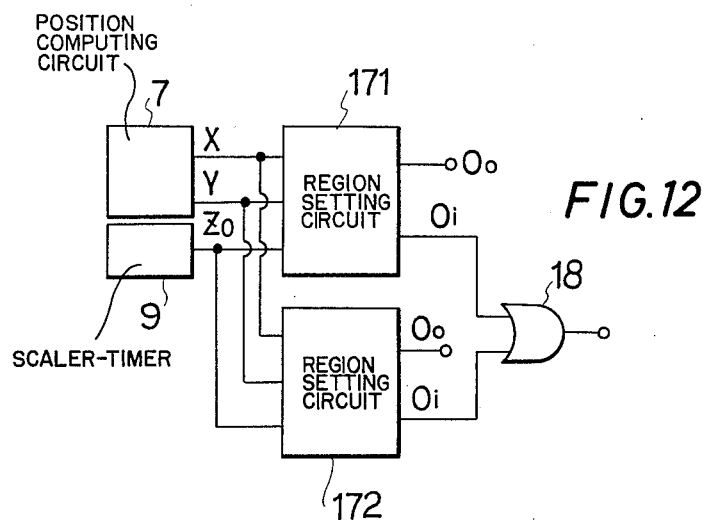
Figure 13:
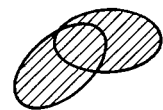
Figure 14:
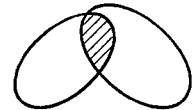

FIG. 12 shows an example of setting such a region. Reference numerals 171 and 172 represent region setting circuits each containing the aforesaid region setting circuits 50, 40, 30 and 20, respectively. These two region setting circuits 171 and 172 are capable of setting regions of interest independently of each other. Reference numeral 18 represents an OR circuit which uses the outputs O₍ᵢ₎ of the region setting circuits 171 and 172 as its inputs. By virtue of this arrangement, it is possible to obtain, as the output signals of the OR circuit 18, outputs corresponding to the coordinate signals X and Y falling within the configuration of the hatched pattern shown in FIG. 13. Also, by replacing the OR circuit 18 of FIG. 12 by an AND circuit, it is possible to derive, as the AND outputs of the AND circuit, the signals falling within the configuration of the hatched pattern shown in FIG. 14. Furthermore, in case the region of interest is required to be set for each of a pair of organs, such as the kidneys, using the region setting circuits 171 and 172, it is possible to set two independent regions for the two kidneys. In that case the outputs O₍ᵢ₎ of the respective region setting circuits 171 and 172 are counted separately and compared with each other. Thus, it is possible to obtain knowledge of that particular part of an organ which has an abnormal condition.

Figure 15:
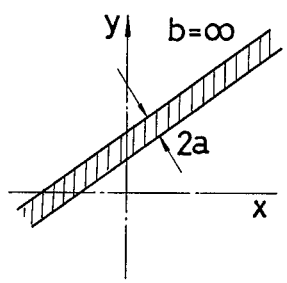
Figure 16:
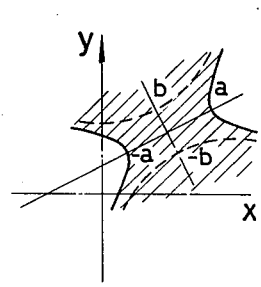
Figure 17:
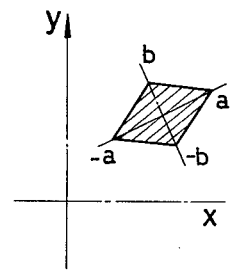

The device according to the present invention is capable of effecting numerous different variations of the configuration of the region of interest to be set. More specifically, in FIG. 6, let one of the values of a and b of the Equation (11) be infinite, i.e. for example, one of the signals X₂/a and Y₂/b is cut off by a switching means. As a result, one of the radii of the ellipse becomes infinite, and thus the setting of a band-shaped region of interest becomes possible. FIG. 15 shows an instance wherein the value b is infinite and shows the setting of a bandshaped region. Next, by either replacing the adder circuit 23 of FIG. 6 by a subtraction circuit, or arranging this adder circuit 23 so as to be replaceable by a subtraction circuit, or by arranging so that an inverting amplifier which receiver the output of the squaring operation circuit 22 may be inserted in the circuit and that this signal to the adder circuit 23 is applied through this amplifier, then the Equations (13) and (14) will become the equations of a hyperbola. Thus, it is possible to effect discrimination with respect to the image area divided into the regions shown in FIG. 16. Furthermore, if the squaring operation circuits 21 and 22 of FIG. 6 are replaced by absolute value circuits or if they are arranged so as to be interchangeable with absolute value circuits, it is possible to set a rhombic region as shown in FIG. 17. Still further, by inserting, in the preceding stage of the comparator circuit 24, an amplifier which is capable of effecting the functional operation of f(X, Y) by expanding the principle of action of the exemplary circuits of the present invention, it becomes possible to set more complicated regions.

FIG. 18 to FIG. 30 show a further example of the device for setting a region of interest for a scintillation camera, according to the present invention. In the device of this instant example, in addition to the provision of circuits for determining whether or not the position of a gamma ray is located within the region of interest, and for counting the number of those gamma rays falling within the region of interest, there is provided a means for displaying, on the monitoring image screen of a monitor oscilloscope, the boundary of the particular region which is being examined.

FIG. 18 is a block diagram of such a device for setting a region of interest as stated above. Reference numeral 173 represents a device for setting a region of interest, numeral 19 represents a counter, numeral 90 represents a control circuit, numeral 100 represents a monitor oscilloscope, and numeral 15 represents a camera oscilloscope. Symbols X and Y represent the signals X and Y for the scintigram which are supplied from the position computing circuit 7 of FIG. 1, respectively. The symbol $Z_O$ represents the unblank signal. From the position computing circuit and the gate of the scintillation camera are supplied 3 signals: a signal X, a signal Y and an unblank signal $Z_O$. In the block diagram of FIG. 18, however, the respective signals are shown by a single signal line. The positions of the luminous spots on both the monitor oscilloscope 100 and the camera oscilloscope 15 are determined by the DC components of the signals X and Y. Using the unblank signal $Z_0$, luminous spots are displayed.

When the region setting circuit 173 is kept inoperative, the scintillation camera is kept operative, and the 3 signals, i.e. the signal X, the signal Y and the unblank signal $Z_0$, are applied to control circuit 90, then luminous spots are produced on both the monitor oscilloscope 100 and the camera oscilloscope 15 at positions determined by the DC components of the inputs X and Y. Here, by actuating the region setting circuit 173, the coordinate signals X and Y are interrupted by the control by circuit 90, and thus it is possible to effect the display of the spots of arbitrary positions on both the monitor oscilloscope 100 and the camera oscilloscope 15, and to display the boundary of the region set by circuit 173 by luminous spots which are brighter than those on the scintillation camera.

The region of interest can be set in the form of a circle or an ellipse of an arbitrary size, and it can also be set at an arbitrary position by parallel translation and rotation of coordinates. The counter 19 counts the number of the luminuous spots which fall within and without the region defined by the region setting circuit 173.

By applying the signal X, the signal Y and the unblank signal $Z_0$, all from the region setting circuit 173, and by actuating the counter 19, the control circuit 90, the monitor oscilloscope 100, and the camera oscilloscope 15, the monitor oscilloscope 100 displays simultaneously both the luminous spots from the scintillation camera and the boundary of the set region which is depicted by luminous spots which are brighter than the abovesaid luminous spots. When the changeover switch S is turned to the contact S-a side, the camera oscilloscope 15 depicts the luminous spots of the scintigram by the signals received from the scintillation camera, and when the changeover switch S is turned to the contact S-b side, it depicts the set region only for that length of time the switch S is switched to the contact S-b side.

FIG. 19 is a detailed block diagram explaining the operation of the device according to the present invention. FIG. 20 shows time charts for the signals in the respective parts of the device. In FIG. 19, the portion enclosed by the one dot chain line represents the region setting circuit 173. This circuit 173 is similar to that shown in FIG. 6 through FIG. 17. Reference numeral 60 represents an oscillator, and reference numeral 70 represents a switching circuit for performing a changeover between the signals X and Y supplied from the position computing circuit 7 of FIG. 1 and the signals supplied from the oscillator 60. Numeral 50 represents a coordinate system shifting circuit, numeral 40 represents a rotation circuit, numeral 30 represents an ellipse radius setting circuit, and numeral 20 represents a circular region setting circuit. These circuits are as previously described. Numeral 80 is a holding circuit for temporarily holding the signal Y from the oscillator circuit 60 via the switching circuit 70.

In order to make the explanation of operation easy, the system will first be described with respect to the case wherein, the coordinate system shifting circuit 50, the rotation circuit 40 and the ellipse radius setting circuit 30 are not in operation, i.e. assuming that a circular region centering around the position of the origin of the rectangular coordinate system on the screen of scintigram is set. The oscillator circuit 60 produces, from its output terminals x and y, an oscillation signal $X_4$ in the form of a step wave signal of 256 steps, and an oscillation signal $Y_4$ in the form of a sine wave signal of 8 kHz (having one cycle of 125 microsecond).

Let us now assume that the output signal of the oscillator circuit 60 has been applied to the circular region setting circuit 20 via the switching circuit 70. The squaring operation circuits 21 and 22 which are contained therein receive at their input side the signals shown in (a) and (b) of FIG. 20, and square them to produce the signals (c) and (d) of FIG. 20, respectively. These signals (c) and (d) are added together by the adder circuit 23 to produce a $X^2+y^2$ signal the waveshape of which is shown by (e) of FIG. 20.

The comparator circuit 24 compares a signal corresponding to the $X^2+Y^2$ signal from the adder circuit 23 value, and produces the a signal shown at (f) of FIG. 20. The holding circuit 80 is controlled by this signal (f) of FIG. 20 so that, by holding for a predetermined length of time the signal $Y_4$ (which is illustrated by (a) of FIG. 20) supplied from the oscillator circuit 60, there is produced a signal shown at (g) of FIG. 20 as its output.

More specifically, the comparator circuit 24 operates so that, for every stepwise variation of the DC level of the signal $X_4$ of the oscillator circuit 60, the comparator circuit 24 detects a value of $Y_4$ such that the sum of the square of the signal $X_4$ and the square of the signal $Y_4$ is always equal to the set value, and circuit 80 holds this value of $Y_4$ for a certain length of time. By connecting the signal $X_4$ (shown by (b) of FIG. 20) from the switching circuit 70 to the X input terminal and the signal which is shown at (g) of FIG. 20 from the holding circuit 80 to the Y input terminal of the monitor oscilloscope 100, and by connecting the unblank signal (shown by (h) of FIG. 20 from the holding circuit 80 to the unblank signal input terminal of the monitor oscilloscope 100, via the control circuit 90, the circle which has been set is depicted.

Figure 21:
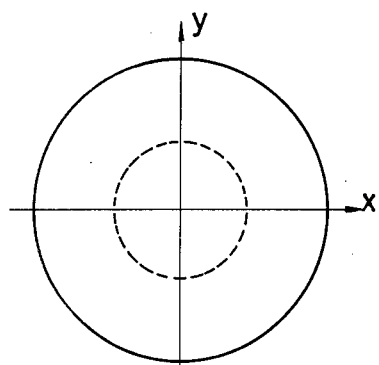

FIG. 21 is an example of the boundary of a circle which is set on the visual field of either the monitor oscilloscope 100 or the camera oscilloscope 15 as depicted with luminous spots shown here by a dotted line. In this example, the image screen of the monitor oscilloscope is comprised of a unit circle which a radius of 1 centered around the origin O of the rectangular coordinated system. Signals $Y_4$ and $X_4$ having the waveshapes of (a) and (b) of FIG. 20, respectively are assumed to be applied to the squaring operation circuits 22 and 21, respectively, and if the reference value for comparison in the comparator circuit 24 is assumed to be 0.25, the sample-held waveshape will become that of (g) of FIG. 20. The relationship between the value of $X_4$, the value of $Y_4$ of the signals which become the luminous spots representing the boundary of the circle set on the monitorscope and $r^2$ will become as shown in Table 1 given below.

Table 1

| $X_4$ | ±0.5 | ±0.4 | ±0.3 | ±0.2 | ±0.1 | 0 |
|---|---|---|---|---|---|---|
| $Y_4$ | 0 | ±0.3 | ±0.4 | ±0.46 | ±0.49 | ±0.5 |
| $r^2$ | 0.25 | 0.25 | 0.25 | 0.25 | 0.25 | 0.25 |

FIG. 21 shows the instance wherein the signals $X_4$ and $Y_4$ of the above-mentioned Table are plotted on the unit circle.

The foregoing statement has been made with respect to the instance wherein only the circular region setting circuit 20 is actuated. However, it is also possible to display in the form of luminous spots in the same way the case in which either one or all of the coordinate system shifting circuit 50, the rotation circuit 40 and the ellipse radius setting circuit 30 is or are actuated.

Figure 22:
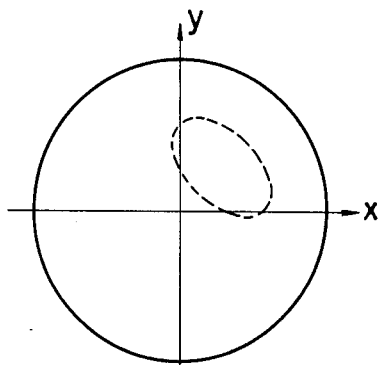

FIG. 22 shows an example of an elliptic region. This is an example of an ellipse having an origin O which has been translated in parallel in the positive directions of both the respective x and y axes, and whose coordinates have been rotated through 45 degrees.

Furthermore, in order to set regions at two sites, it is only necessary to prepare, in two sets, the coordinate system shifting circuit 50, the rotation circuit 40, the ellipse radius setting circuit 30 and the circular region setting circuit 20. By providing these circuits in two sets, it becomes possible to form two set regions at two independent sites. In the event that there is an overlap between the two regions, it is possible to set an OR region or an AND region of the two regions by processing them with an OR circuit or an AND circuit.

Figure 23:
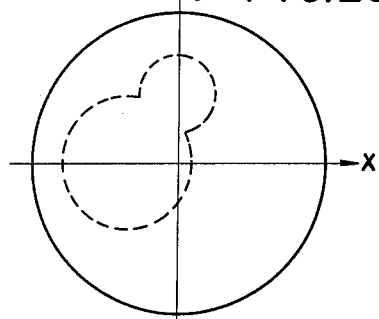
Figure 24:
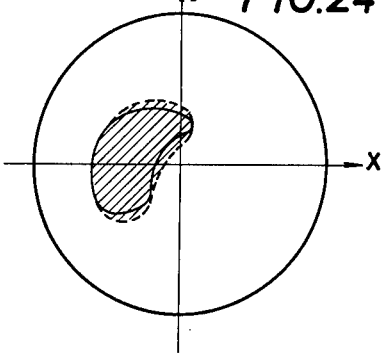
Figure 25:
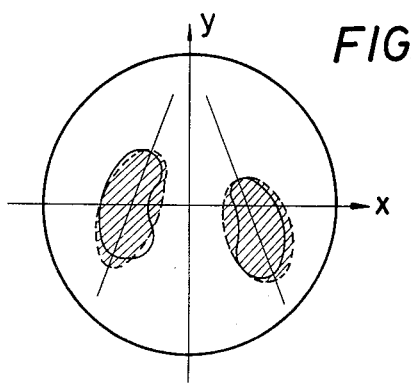

FIG. 23 is an example showing the OR region when two circles overlap each other locally. FIG. 24 is an example showing the OR region (the hatched portion enclosed by broken line) when two ellipses overlap each other locally. The solid line of FIG. 24 shows the configuration of the liver of a human being. It has been difficult in the past to set a region for the liver having a configuration close to that of the actual liver. According to the present invention, however, it becomes possible to realize a closely resembling configuration by virtue of the OR regions of two ellipses as shown in FIG. 24.

Also, in case regions are set over the kidneys, the setting becomes easy by inclining the regions relative to the vertical by rotation of coordinates.

Next, let us return to FIG. 19. In order to count the luminous spots which fall within the set region, the signals X and Y supplied from the position computing circuit 7 are applied to the input side of the coordinate system shifting circuit 50 via the switching circuit 70 to conduct the required operation and the gate of the counter 19 is opened and closed by the output $O_i$ of the circular region setting circuit which indicates the location is within the region, to count the unblank signal $Z_O$ supplied from the scintillation camera.

Figure 26:
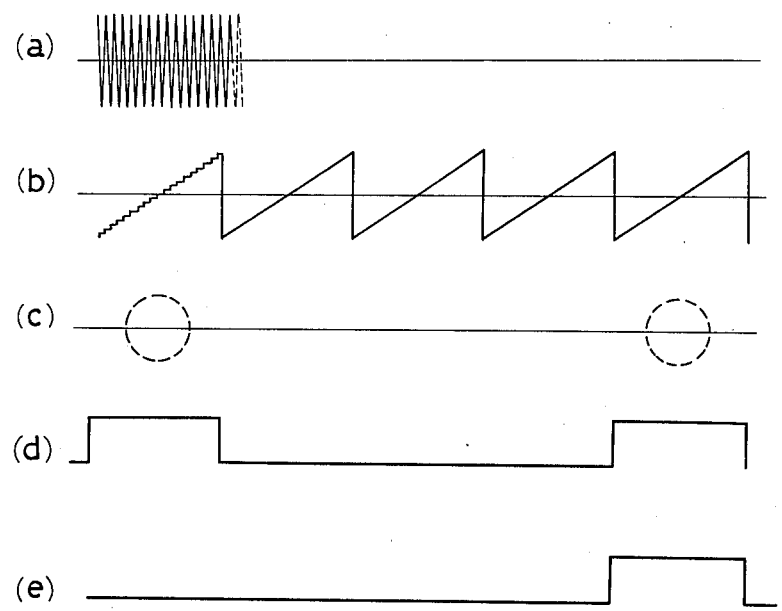

FIG. 26 shows the timing charts of the signal of the switching circuit 70 and the control signal of the control circuit 90 when the luminous spots of the scintillation camera and the luminous spots of the boundary of the set region are displayed simultaneously on the monitorscope 100. FIG. 26 (a) and (b) represent the signal $Y_4$ and the signal $X_4$ respectively which are generated by the oscillator circuit 60. FIG. 26 (c) represents the signal y which is held by the holding circuit 80 and is produced from the output terminal 80A thereof. FIG. 26 (d) represents a high level signal when the set region is displayed. In the switching circuit 70, this signal controls the operation of connecting or not connecting the output of the oscillator circuit 60 to the coordinate system shifting circuit 50. In the control circuit 90, this signal controls the operation of connecting or not connecting the signal x, the signal y and the unblank signal on the input side to the monitor oscilloscope 100. When (d) is of a low level, the signals X and Y from the position computing circuit 7 are connected to the coordinate system shifting circuit 50, and the signals X and Y and the unblank signal $Z_0$ are connected to the monitor oscilloscope 100. As a result, the luminous spots of the scintillation camera are displayed on the monitor oscilloscope 100. At the same time therewith, the counter 19 is actuated to count the luminous spots which fall within the region and those which fall outside of the region. FIG. 26 (e) represents a switching signal for turning the cameraoscilloscope 15 on. The signal x from the switching circuit 70 and the signal y from the holding circuit 80 and the unblank signal $Z_0$ are connected to the camera oscilloscope 15 which normally is connected to the scintillation camera via the control circuit 90, only when the switching signal (e) is caused to have a a high level, to thereby cause the camera oscilloscope 15 to depict the boundary of the a region on the image-producing screen for only a certain length of time. By attaching a camera to the camera oscilloscope 15 and keeping the diaphragm open, and by operating in the manner as stated above, there is obtained a scintigram which displays the boundary.

Figure 27:
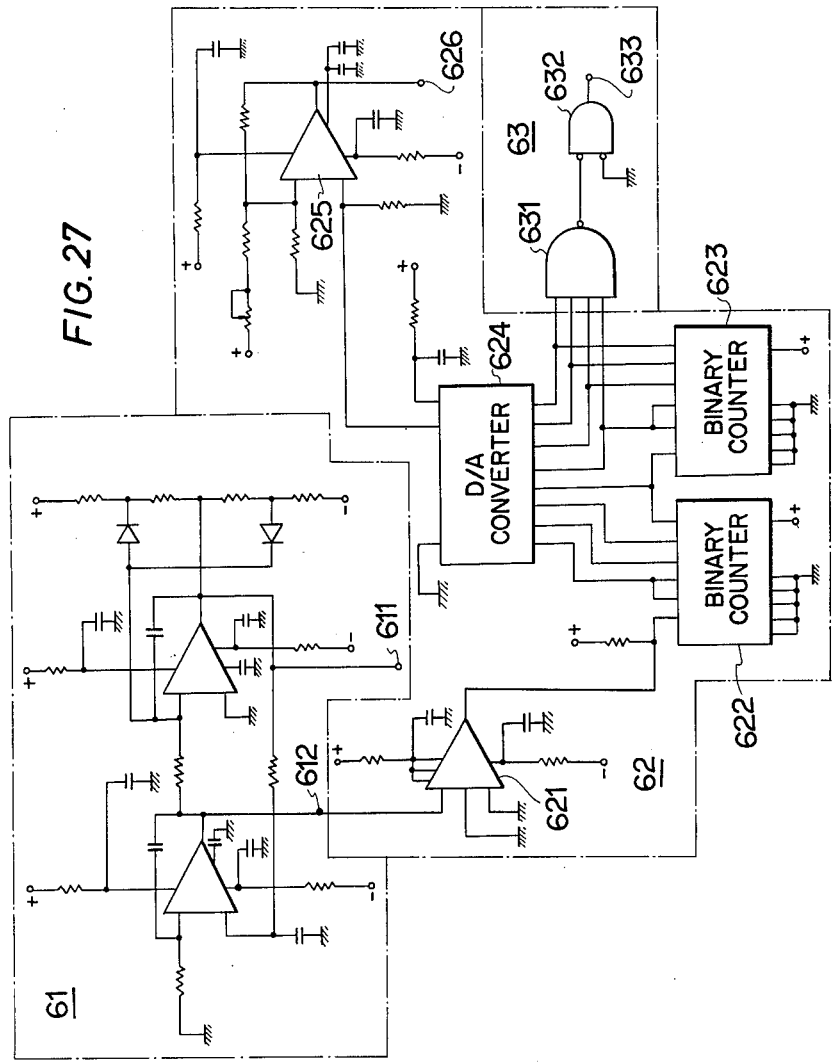

Next, a description will be made with respect to a concrete example of the oscillator circuit 60 shown in FIG. 19, by referring to FIG. 27. The oscillator circuit 60 is comprised of an oscillator 61 for generating a sine wave of 8 kHz as shown in (a) of FIG. 20, a signal forming circuit 62 for producing a wave signal $X_4$ shown in (b) of FIG. 20, and a switching forming circuit 63 for forming an ROI (Region of Interest) switching signal indicating whether or not the boundary of the set region is to be displayed by luminous spots. The oscillator 61 is arranged so that, in addition to generating the signal $Y_4$, it also generates a signal which is 180 degrees delayed in phase than the signal $Y_4$. Numeral 611 represents the output terminal for the signal $Y_4$. Numeral 612 represents the output terminal for the signal which is 180 degrees delayed in phase than the signal $Y_4$. In the $X_4$ signal forming circuit 62, an output pulse is generated by the comparator 621 only when the signal from said output terminal 612 has a potential higher than zero, and this output pulse from the comparator 621 is counted by the binary counters 622 and 623 in a cascade connection. More specifically, the output of the top bit of the binary counter 622 is received by the input section of the binary counter 623. The outputs of the binary counters 622 and 623 are applied to a D/A converter 624 in which the outputs are converted into an analog signal. The step wave which is the output from the D/A converter 624 is amplified by an operational amplifier 625 and appears at the output terminal 626. The NAND circuit 631 of the ROI switching signal forming circuit 63 uses the outputs from the four upper bits of the binary counter 623 as its inputs, and produces a ROI switching signal of "0" when all of the signals of these bits are "1". When the NAND circuit 631 has an output of "0", the inverting circuit 632 produces a ROI switching signal of "1" from the output terminal 633.

Figure 28:
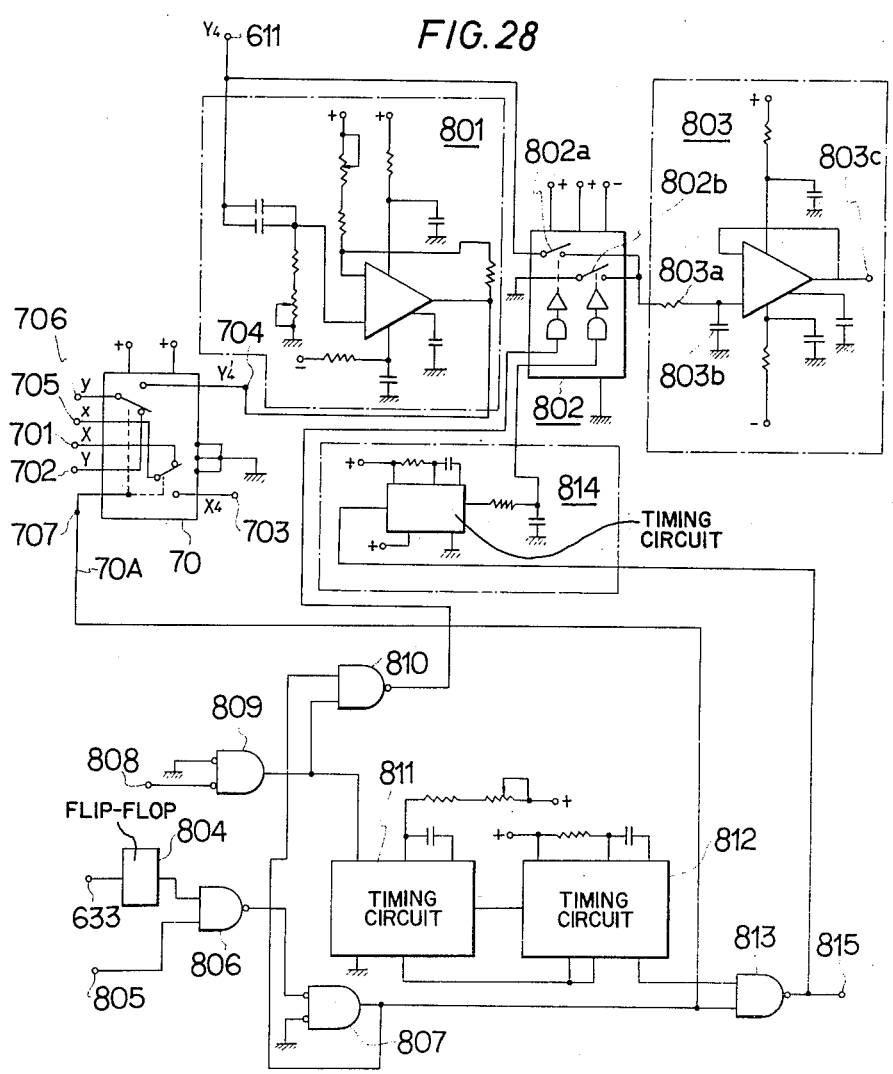

FIG. 28 shows a concrete example of the switching circuit 70 and the holding circuit 80 shown in FIG. 19. In FIG. 28, those portions other than the switching circuit 70 constitute the holding circuit. The switching circuit 70 has a signal X input terminal 701 and a signal Y input terminal 702, those signals being supplied from the position computing circuit 7, a signal $X_4$ input terminal 703 and a signal $Y'_4$ input terminal 704, said signal $Y'_4$ being obtained by advancing the phase of the signal $Y_4$ which, together with the signal $X_4$, is supplied from the oscillator circuit 60, an output terminal 705 for applying either the signal X or the signal $X_4$ to the coordinate system shifting circuit 50, and an output terminal 706 for applying either the signal Y or the signal $Y'_4$ to the coordinate system shifting circuit 30. The switching is controlled by a switching signal 70A (ROI display signal) which is applied to a switching signal input terminal 707. Numeral 611 represents the output terminal of the oscillator 61 also shown in FIG. 27. The signal $Y_4$ which is a sine wave of 8 kHz as stated above appears at this terminal. Numeral 801 represents a phase advancing circuit for forming the signal $Y'_4$ by advancing the phase of the signal $Y_4$. This phase advancing circuit is provided to compensate if the signal $Y_4$ is delayed during its passage through the coordinate system shifting circuit 50, the rotation circuit 40, the ellipse radius setting circuit 30, and the squaring operation circuit 22 and the adder circuit 23 provided in the circular region setting circuit 20 which are all shown in FIG. 19, and that when the signal $Y_4$ arrives at the comparator circuit 24, it has been delayed in phase. This phase advancing circuit operates so as to advance the phase of the signal $Y_4$ by an amount corresponding to the delay time arising within the aforesaid respective circuits during its passage therethrough. Numeral 802 represents a switching circuit and numeral 803 represents an amplifier for causing the holding operation of the signal $Y_4$. Numeral 633 represents the output terminal of the ROI switching signal forming circuit 63 shown in FIG. 27. Every time that a pulse of "1" is applied from this output terminal 633 to the flip-flop 804, the output of this flip-flop 804 is inverted. Numeral 805 represents an ROI monitoring signal input terminal which is supplied with a signal of "1" for indicating the boundary of the set region when a switch (not shown) is operated manually. When the ROI monitoring signal has a level of "1", for every alternate changeover action between "1" and "0" of the output signal of the flip-flop 804, the NAND circuit 806 switchs between "0" and "1". In accordance therewith, the inverting circuit 807 switchs between "1" and "0". The output signal of this inverting circuit 807 serves as the switching signal 70A of the switching circuit 70. When this switching signal 70A is "1", the switching circuit 70 is controlled, so that a connection is established between the terminals 704 and 706, and also between the terminals 703 and 705, respectively. When the switching signal 70A becomes "0", the state of connections illustrated is produced, i.e. a connection is established between the terminals 701 and 705, and between the terminals 702 and 706.

Numeral 808 represents a terminal for receiving the detection signal which is delivered from the comparator circuit 24 shown in FIG. 6 when this comparator circuit 24 has detected the agreement between the output signal from the adder circuit 23 and the reference voltage. This time of agreement which is to be detected can be the time at which the output signal from the comparator circuit 24 changes from "0" to "1" or from "1" to "0". In this instant example, the latter is used. The detection signal at the time of agreement becomes "0". The length of this "0" signal is about 1 microsecond, and this signal is formed by a circuit not shown. The output signal of the inverting circuit 809 becomes "1" when the detection signal by said comparator circuit is "0". Therefore, when the detection signal "0" is applied to the terminal 808 during the period in which the output signal (ROI display signal) of the aforesaid inverting circuit 807 remains "1", the output signal of the NAND circuit 810 becomes "0", thereby the switching element 802a is instantaneously rendered on. At that time, the capacitor 803b is charged through a resistor 803a by the signal $Y_4$. On the other hand, when the output signal of the inverting circuit 809 becomes "1", this signal is applied to a timing circuit 811. The output signal of this timing circuit 811 is applied to another timing circuit 812. Whereby, the output signal of the timing circuit 812 will become "1" after a delay of about 1 microsecond after the output signal of the inverting circuit 809 has become "1". By causing this state of "1" to be held for an appropriate length of time, the output signal of the NAND circuit 813 is made "0" throughout this length of time. This signal of "0" from the NAND circuit 813 is applied to the control section of the switching element 802b via a delay circuit 814. Whereby, the switching element 802b is closed after a predetermined length of time following the opening of the switching element 802a. Accordingly, the voltage of the capacitor 803b which has been charged up via the resistor 803a by the signal $Y_4$ is held only for the time from the opening of the switching element 802a till the closure of the switching element 802b. Thus, the voltage of the signal $Y_4$ at the time that the comparator circuit 24 has detected from the output terminal 803c the inversion from the state of $X_3^2+Y_3^2 \sqrt{E}$ to the state of $X_3^2+Y_3^2 < E$ is held. By repeating this operation for every half cycle of the signal $Y_4$, there is obtained a signal as shown at (g) of FIG. 20 at the output terminal 803c. The inverted signal of the output of the NAND circuit 813 is used as an unblank signal for indicating the boundary.

Figure 29:
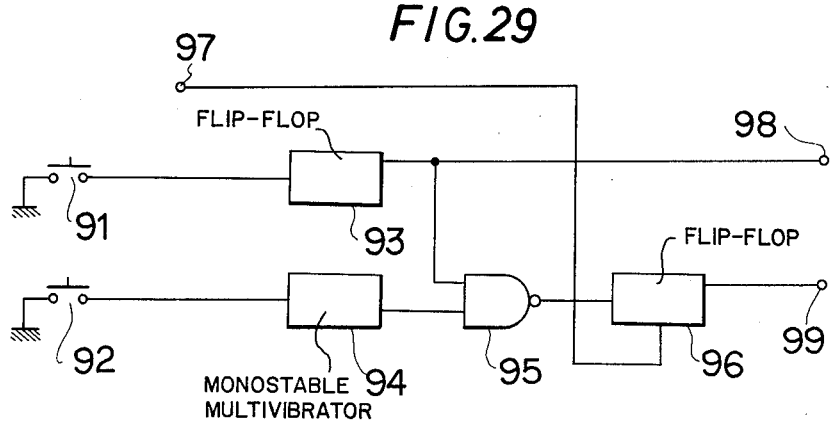

FIG. 29 shows an example of the circuit for generating an ROI monitor signal which is applied to the terminal 805 shown in FIG. 28 and an ROI camera signal for causing the camera oscilloscope 15 to indicate a boundary. In FIG. 29, numeral 91 represents a manual switch switched by the operator for causing the monitor oscilloscope 100 to indicate a boundary. Numeral 92 represents a manual switch switched by the operator for causing the camera oscilloscope 15 to indicate a boundary. Numeral 93 represents a flip-flop for generating a "1" at its output when the manual switch 91 is turned on. An ROI monitoring signal is obtained at the output terminal 98 of this flip-flop. Numeral 94 represents a monostable multi-vibrator which operates so that, when the manual switch 92 is turned on, it generates a single rectangular wave signal. Numeral 95 represents a NAND circuit. Numeral 96 represents a flip-flop. When the monostable multi-vibrator 94 is rendered on while the flip-flop 93 is set, the output of the NAND circuit 95 turns off, and sets the flip-flop 96, and an ROI camera signal is produced by the output terminal 99. This ROI camera signal becomes a control signal for applying an unblank signal to the camera oscilloscope 15 for causing it to indicate the boundary. The ROI camera signal is re-set by the build-up of an inverted signal of the ROI display signal (the output signal of the AND circuit 807 of FIG. 28) which is received from the terminal 97.

FIG. 30 shows the summary of the behaviors of this device for setting a region of interest which is equipped with a boundary indicating function. As will be apparent from FIG. 30, during the period in which an ROI monitoring signal is applied to the terminal 805 of FIG. 28 as shown by (d) of FIG. 30, the ROI display signal shown by (f) of FIG. 30 is alternately changed over. Therefore, the switching circuit 70 is changed over alternately, with the time T as one cycle. Whereby, the input signal of the adder circuit 23 in the circular region setting circuit is alternately changed over by the signals prepared based on X and Y and by the signals prepared on the basis of $X_4$ and $Y'_4$ as shown at (g) and (h) of FIG. 30. Accordingly, the signals of (i) to (l) of FIG. 30 also are signals which are alternately changed over. By the fact that an ROI camera signal as shown at (e) of FIG. 30 is generated from the circuit shown in FIG. 29, an unblank signal as shown at (m) of FIG. 30 is applied to the camera oscilloscope to thereby indicate the boundary of the set region by luminous spots. It will be apparent that by photographying the image which is the superposed representation of an image indicating this set region and an image prepared based on the signals X and Y prior to the display of said image of the set region by luminous spots, there can be obtained a photographic image which bears an indication of the boundary.

What is claimed is:

1. A device for setting a region of interest for a scintillation camera for obtaining a photographic image which is comprised of luminous spots corresponding to the positions of incident gamma rays, from coordinate signals X and Y representing the positions of the incident gamma rays and from a signal Z proportional to the energies of the incident gamma rays, wherein said device includes a circular region setting circuit for discriminating whether or not said coordinate signals are located within a predetermined region of interest by comparing the sum of the squares of the respective coordinate signals X and Y with a predetermined value.

2. A device according to claim 1, in which said circular region setting circuit comprises: a first squaring circuit for squaring the coordinate signal X, a second squaring circuit for squaring the coordinate signal Y; an adder circuit for summing the output signals from the respective squaring circuits; a reference voltage generating circuit for generating an arbitrary reference voltage; and a comparator circuit for comparing the output signals from said adder circuit and said reference voltage generating circuit and for generating a first output signal when the potential of the output signal from said adder circuit is lower than the reference voltage and for generating a second output signal when the potential of the output signal from said adder circuit is higher than said reference voltage.

3. A device according to claim 2, in which said circular region setting circuit further comprises: an energy recognition circuit receiving the signal Z for producing an unblank signal $Z_0$ when the signal Z indicates the energy of the incident gamma rays fall within a predetermined range; and an inverting circuit for inverting said first output signal, and an AND circuit for producing an output upon receipt of both said output from said inverting circuit and said unblank signal $Z_0$.

4. A device according to claim 3, in which said circular region setting circuit further comprises: an AND circuit for producing an output upon receipt of both said second output signal and said unblank signal $Z_0$.

5. A device for setting a region of interest for a scintillation camera for obtaining a photographic image which is comprised of luminous spots corresponding to the positions of incident gamma rays, from coordinate signals X and Y representing the positions of the incident gamma rays and from a signal Z proportional to the energies of the incident gamma rays, and for discriminating whether or not the coordinate signals X and Y which represent the positions of the incident gamma rays fall within a region of interest set on a rectangular coordinate system provided on the visual field of the camera, wherein said device includes at least one set of circuits each set comprising: a coordinate signal shifting circuit for shifting the coordinate signals X and Y in their positions parallel to the axes of the rectangular coordinate system; a rotational circuit for rotating the output coordinate signals from said coordinate signal shifting circuit centering around the origin of the coordinates; an ellipse radius setting circuit for dividing the output coordinate signals by values a and b, respectively, a and b being manually selected predetermined constants; and a circular region setting circuit for forming the sum of the squares of the output coordinate signals of said ellipse radius setting circuit and for comparing the potential of this sum with a predetermined reference voltage to determine whether the coordinate signals X and Y are located within a predetermined region.

6. A device according to claim 5, in which: said circular region setting circuit comprises: first and second squaring operation circuits for squaring said coordinate signals X and Y to convert them to signals $X^2$ and $Y^2$, respectively; an adder circuit for summing said signals $X^2$ and $Y^2$ to convert them to a signal $X^2+Y^2$; a reference voltage generating circuit for generating a reference voltage E; and a comparator circuit for comparing said output signal $X^2+Y^2$ of said adder circuit with said reference voltage E and for generating a first output signal when the potential of said output signal $X^2+Y^2$ of said adder circuit is less than the reference voltage E, and for generating a second output signal when the potential of said output signal $X^2+Y^2$ of said adder circuit is greater than the reference voltage E.

7. A device according to claim 6, in which: said circular region setting circuit further comprises: an AND circuit for taking an AND of said signal Z proportional to the energies of the incident gamma rays and said second output signal; an inverting circuit for inverting said first output signal; and an AND circuit for taking an AND of said signal Z and the output signal of said inverting circuit.

8. A device as claimed in claim 6 further comprising:
a subtraction circuit having two inputs and an output for generating an output signal whose voltage is the difference in voltage between the input signals; and
a selective subtraction means for selectively replacing said adder circuit with said subtraction circuit.

9. A device as claimed in claim 6 further comprising:
a selective inverter means for selectively inverting the output of at least one of said squaring operation circuits.

10. A device as claimed in claim 6 further comprising:
a pair of absolute value circuits for producing a positive signal having the same magnitude as the absolute value of the input applied thereto; and
a selective absolute value means for selectively replacing said squaring operation circuits with said absolute value circuits.

11. A device according to claim 5, in which: said coordinate signal shifting circuit comprises a reference signal generating circuit for generating coordinate signals $-X_0$ and $-Y_0$ associated with newly set reference coordinates prepared from said rectangular coordinate system; and adder circuits for summing the coordinate signals X, Y and said signals $-X_0$, $-Y_0$ to convert them to signals $X-X_0$ and $Y-Y_0$, respectively.

12. A device according to claim 11, in which: said circular region setting circuit further comprises: an amplifier for conducting functional computation of the output from said rotation circuit by a predetermined function f(X, Y).

13. A device according to claim 5, in which: said rotation circuit comprises a voltage divider for computing a signal (X') $\cos\theta$ from the output signal X' of the coordinate signal shifting circuit; a voltage divider for computing a signal (Y') $\cos\theta$ from said output signal Y' of the coordinate signal shifting circuit; a voltage divider for computing a signal (X') $\sin\theta$ from the signal X'; a voltage divider for computing a signal (Y') $\sin\theta$ from the signal Y'; an inverting circuit for inverting the signal (X') $\sin\theta$ to output a signal $-(X')$ $\sin\theta$; an adder circuit for summing the signals (X') $\cos\theta$ and (Y') $\sin\theta$ to convert them to a signal (X') $\cos\theta=(Y')$ $\sin\theta$; and an adder for summing the inverted signal $-(X')$ $\sin\theta$ and the signal (X') $\cos\theta$ to output a signal $-(X')$ $\sin\theta+(Y')$ $\cos\theta$, wherein $\theta$ is a manually selected predetermined constant.

14. A device according to claim 5, in which: said ellipse radius setting circuit comprises division circuits for converting the output signals X'' and Y'' of said rotation circuit to signals X''/a and Y''/b, respectively, wherein a and b are manually selected predetermined constants.

15. A device according to claim 14, in which: said ellipse radius setting circuit further comprises output selection means for selectively interrupting either one of the outputs X'''/a and Y'''/b.

16. A device according to claim 5, in which: said coordinate signal shifting circuit comprises reference signal generating circuits for generating coordinate signals $-X_0$ and $-Y_0$ associated with newly set reference coordinates prepared from said rectangular coordinate system, and adder circuits for summing the coordinate signals X and Y and said signals $-X_0$ and $-Y_0$ to convert them to signals $X-X_0$ and $Y-Y_0$, respectively; said rotation circuit comprises a voltage divider for computing a signal $(X-X_0)\cos\theta$ from the output signal $X-X_0$ of the coordinate signal shifting circuit, a voltage divider for computing a signal $(Y-Y_0)\cos\theta$ from said output signal $Y-Y_0$ of the coordinate signal shifting circuit, a voltage divider for computing a signal $(X-X_0)\sin\theta$ from the signal $X-X_0$, a voltage divider for computing signal $(Y-Y_0)\sin\theta$ from the signal $Y-Y_0$, an inverting circuit for inverting the signal $(X-X_0)\sin\theta$ to output a signal $-(X-X_0)\sin\theta$, an adder circuit for summing the signals $(X-X_0)\cos\theta$ and $(Y-Y_0)\sin\theta$ to convert them to a signal $(X-X_0)\cos\theta+(Y-Y_0)\sin\theta$; and an adder for summing the inverted signal $-(X-X_0)\sin\theta$ and the signal $(Y-Y_0)\cos\theta$ to output a signal $-(X-X_0)\sin\theta+(Y-Y_0)\cos\theta$ wherein $\theta$ is a manually selected predetermined constant; and said ellipse radius setting circuit comprises first and second division circuits for converting the signals $(X-X_0)\cos\theta+(Y-Y_0)\sin\theta$ and $-(X-X_0)\sin\theta+(Y-Y_0)\cos\theta$ of said rotation circuit to signals $[(X-X_0)\cos\theta+(Y-Y_0)\sin\theta]/a$ and $[-(X-X_0)\sin\theta+(Y-Y_0)\cos\theta]/b$, respectively, wherein a and b are manually selected predetermined constants; and said circular region setting circuit comprises first and second squaring operation circuits for squaring said coordinate signals $[(X-X_0)\cos\theta+(Y-Y_0)\sin\theta]/a$ and $[-(X-X_0)\sin\theta+(Y-Y_0)\cos\theta]/b$ to convert them to signals $[(X-X_0)\cos\theta+(Y-Y_0)\sin\theta]^2/a$ and $[-(X-X_0)\sin\theta+(Y-Y_0)\cos\theta]^2/b^2$, respectively, an adder circuit for summing said signals $[(X-X_0)\cos\theta+(Y-Y_0)\sin\theta]^2/a^2$ and $[-(X-X_0)\sin\theta+(Y-Y_0)\cos\theta]^2/b^2$ to convert them to a signal $[(X-X_0)\cos\theta+(Y-Y_0)\sin\theta]^2/a^2+[-(X-X_0)\sin\theta+(Y-Y_0)\cos\theta]^2/b^2$, a reference voltage generating circuit for generating a reference voltage E, and a comparator circuit for comparing said output signal $[(X-X_0)\cos\theta+(Y-Y_0)\sin\theta]^2/a^2+[-(X-X_0)\sin\theta+(Y-Y_0)\cos\theta]^2/b^2$ of said adder circuit with said reference voltage E and for generating a first output signal when the potential of said output signal $[(X-X_0)\cos\theta+(Y-Y_0)\sin\theta]^2/a^2+[-(X-X_0)\sin\theta+(Y-Y_0)\cos\theta]^2/b^2$ of said adder circuit is less than with the reference voltage E, and for generating a second output signal when the potential of said output signal $[(X-X_0)\cos\theta+(Y-Y_0)\sin\theta]^2/a^2+[-(X-X_0)\sin\theta+(Y-Y_0)\cos\theta]^2/b^2$ of said adder circuit is greater than the reference voltage E.

17. A device according to claim 5 comprising a first set of circuits and a second set of circuits, further comprising an OR circuit connected to said circular region setting circuit of said first set and said circular regional setting circuit of said second set for producing an output when said coordinate signals X and Y are located within at least one predetermined region of said first set and said second set.

18. A device according to claim 5 comprising a first set of circuits and a second set of circuits, further comprising an AND circuit connected to said circular region setting circuit of said first set and said circular region setting circuit of said second set for producing an output when said coordinate signals X and Y are located within the predetermined regions of both said first set and said second set.

19. A device for setting a region of interest for a scintillation camera for obtaining a photographic image which is comprised of luminous spots corresponding to the positions of incident gamma rays, from coordinate signals X and Y representing the positions of the incident gamma rays and from a signal Z proportional to the energies of the incident gamma rays, wherein said device includes at least one set of circuits each set comprising: an oscillator circuit for generating oscillating coordinate signals $X_4$ and $Y_4$ in which $X_4$ moves stepwise through the possible X coordinate values and $Y_4$ oscillates through the possible Y coordinate values during each step of $X_4$; a switching circuit for changing over said oscillating coordinate signals with said coordinate signals X and Y; a coordinate signal shifting circuit for causing the signals from said switching circuit to make a predetermined parallel translation on a pre-set rectangular coordinate system; a rotational circuit for causing the signals generated by said coordinate signal shifting circuit to rotate and move centering around the origin of said rectangular coordinate system a predetermined amount; an ellipse radius setting circuit for conducting division of each of the signals from said rotation circuit by arbitrarily selected values; first and second squaring operation circuits for generating a signal corresponding to the square of each of the signals from said ellipse radius setting circuit; an adder circuit for summing the signals generated by said squaring operation circuits; a reference voltage means for generating a predetermined reference voltage; a comparator circuit for comparing the potential of the output signal of said adder circuit with said predetermined reference voltage from said reference voltage means, for generating a first output signal when the output of said adder circuit equals said predetermined reference voltage and for generating a second output signal when the output of said adder circuit is less than said predetermined reference voltage; a holding circuit receiving said oscillating coordinate signal $Y_4$ and said first output signal from said comparator circuit for holding for a predetermined length of time said oscillation signal $Y_4$ when said first output signal is received from said comparator circuit; a first unblank signal generating circuit connected to said holding circuit and said comparator circuit for generating a first unblank signal after receiving said first output signal during the period when said holding circuit holds said oscillating coordinate signal; and said device further comprising a display means connected to the switching circuit of said set of circuits and receiving said first output signals from said comparator circuit for displaying on a rectangular coordinate system the coordinate signals from said switching circuit when said switching circuit is switched to said oscillating coordinate signals $X_4$ and $Y_4$ and said first output signal is received and when said swtiching circuit is switched to the coordinate signals X and Y; and a counting circuit connecting to the switching circuit of said set of circuits and receiving said second output signal from said comparator circuit for counting the number of times said second output signal is received when said switching circuit is switched to the coordinate signals X and Y.

20. A device according to claim 19, in which: said oscillator circuit comprises: an oscillating means for generating a sine wave oscillation signal $Y_4$; and means for converting said oscillation signal $Y_4$ to a rectangular wave, for digitally counting said rectangular wave and for digital to analog converting the resulting count output to obtain an oscillation signal $X_4$ which is a stepped wave.

21. A device according to claim 19, in which: said coordinate signal shifting circuit is comprised of reference signal generating circuits for generating coordinate signals $-X_0$ and $-Y_0$ associated with newly set reference coordinates prepared from said rectangular coordinate system; and adder circuits for summing the coordinate signals X and Y and said signals $-X_0$, $-Y_0$ to convert them to signals $X-X_0$ and $Y-Y_0$, respectively; said rotation circuit is comprised of a voltage divider for computing a signal $(X-X_0) \cos \theta$ from the output signal $X-X_0$ of the coordinate signal shifting circuit, a voltage divider for computing a signal $(Y-Y_0) \cos \theta$ from said output signal $Y-Y_0$ of the coordinate signal shifting circuit, a voltage divider for computing a signal $(X-X_0) \sin \theta$ from the signal $X-X_0$, a voltage divider for computing a signal $(Y-Y_0) \sin \theta$ from the signal $Y-Y_0$, an inverting circuit for inverting the signal $(X-X_0) \sin \theta$ to output a signal $-(X-X_0) \sin \theta$, an adder circuit for summing the signals $(X-X_0) \cos \theta$ and $(Y-Y_0) \sin \theta$ to convert them to a signal $(X-X_0) \cos \theta + (Y-Y_0) \sin \theta$; and an adder for summing the inverted signal $-(X-X_0) \sin \theta$ and the signal $(Y-Y_0) \cos \theta$ to output a signal $-(X-X_0) \sin \theta + (Y-Y_0) \cos \theta$, wherein $\theta$ is a manually selected predetermined constant; and said ellipse radius setting circuit comprises division circuits for converting the signals $(X-X_0) \cos \theta + (Y-Y_0) \sin \theta$ and $-(X-X_0) \sin \theta + (Y-Y_0) \cos \theta$ of said rotation circuit to signals $[(X-X_0) \cos \theta + (Y-Y_0) \sin \theta]/a$ and $[-(X-X_0) \sin \theta + (Y-Y_0) \cos \theta]/b$, respectively, wherein a and b are manually selected predetermined constants.

22. A device according to claim 19, further comprising: a circuit for adjusting the phase of the oscillating coordinate signal which is applied to said coordinate signal shifting circuit to compensate for the delay times in said coordinate signal shifting circuit, said ellipse radius setting circuit, said squaring operation circuit, and said adder circuit.

23. A device according to claim 19, further comprising: an actuator circuit for the switching circuit, said actuator circuit comprising: a pulse generator circuit including a counter connected to said oscillator circuit for counting said $Y_4$ oscillating coordinate signal and for generating a pulse when the number stored in said counter has reached a predetermined value; a flip-flop receiving said pulse from said counter for inverting said pulse whenever this pulse is applied thereto; a command signal means for producing a command signal to indicate the specified region of interest when manually actuated; and a gate circuit receiving said command signal and the output of said flip-flop for generating an output upon receipt of both said command signal and said output from said flip-flop, said switching circuit being actuated by the output signal from said gate circuit to conduct said change-over action.

24. A device as claimed in claim 19, wherein said holding circuit comprises: a level detecting circuit connected to said oscillator circuit for generating a pulse whenever said oscillating coordinate signal $X_4$ reaches a predetermined value; a flip-flop circuit connected to said level detecting circuit for inverting the output of said level detecting circuit; a command signal means for producing a command signal to indicate the specified region of interest when manually actuated; a gate circuit connected to said flip-flop circuit and said command signal means for generating an output when both the output of said flip-flop circuit and said command signal is received; a storage element for storing said oscillating coordinate signal $Y_4$; a first switching element for initiating the storage operation of said storage element; a second switching element for releasing the storage operation of said storage element; a storage control circuit connected to said gate circuit, said comparator circuit and said first switching element for driving said first switching element upon receipt of both said output of said gate circuit and said first output signal of said comparator circuit; and a storage release control circuit connected to said comparator circuit and said second switching element for driving said second switching element a predetermined length of time after receipt of said first output signal.

25. A device according to claim 24, further comprising: circuits for generating pulse signals which cause a delay in the detection signal of said comparator circuit for a predetermined length of time; and a circuit for generating said first unblank signal for obtaining said image of said specified region which is to be indicated, whenever there exist an output signal of the first-occurring circuits and an output signal of said gate circuits.

* * * * *